United States Patent
Burbank et al.

(10) Patent No.: US 8,219,182 B2
(45) Date of Patent: *Jul. 10, 2012

(54) CAVITY-FILLING BIOPSY SITE MARKERS

(75) Inventors: Fred H. Burbank, Laguna Niguel, CA (US); Paul Lubock, Laguna Niguel, CA (US); Michael L. Jones, San Clemente, CA (US)

(73) Assignee: Senorx, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/852,286

(22) Filed: Aug. 6, 2010

(65) Prior Publication Data

US 2010/0324416 A1 Dec. 23, 2010

Related U.S. Application Data

(63) Continuation of application No. 10/990,327, filed on Nov. 16, 2004, now Pat. No. 7,792,569, which is a continuation of application No. 10/124,757, filed on Apr. 16, 2002, now Pat. No. 6,862,470, which is a continuation-in-part of application No. 09/717,909, filed on Nov. 20, 2000, now Pat. No. 6,725,083, which is a continuation-in-part of application No. 09/343,975, filed on Jun. 30, 1999, now Pat. No. 6,347,241, which is a continuation-in-part of application No. 09/241,936, filed on Feb. 2, 1999, now Pat. No. 6,161,034.

(51) Int. Cl.
*A61B 8/00* (2006.01)
*A61B 6/00* (2006.01)
*A61B 8/14* (2006.01)

(52) U.S. Cl. ........ 600/431; 600/414; 600/420; 600/426; 600/458

(58) Field of Classification Search .................. None
See application file for complete search history.

(56) References Cited

U.S. PATENT DOCUMENTS

| | | | |
|---|---|---|---|
| 2,192,270 A | 3/1940 | McGowan |
| 2,481,408 A | 9/1949 | Fuller et al. |
| 2,832,888 A | 4/1958 | Houston |
| 2,899,362 A | 8/1959 | Sieger, Jr. et al. |
| 2,907,327 A | 10/1959 | White |
| 3,341,417 A | 9/1967 | Sinaiko |
| 3,402,712 A | 9/1968 | Eisenhand |
| 3,516,412 A | 6/1970 | Ackerman |

(Continued)

FOREIGN PATENT DOCUMENTS

DE 1029528 B 5/1958

(Continued)

OTHER PUBLICATIONS

Armstrong, J.S., et al., "Differential marking of Excision Planes in Screened Breast lesions by Organically Coloured Gelatins", Journal of Clinical Pathology, Jul. 1990, No. 43 (7) pp. 604-607, XP000971447 abtract; tables 1,2.

(Continued)

*Primary Examiner* — Joseph M Pelham

(57) ABSTRACT

An ultrasound-detectable biopsy marker mass has a detectable in-vivo lifetime during which the marker mass remains readily detectable by ultrasound imaging. The ultrasound-detectable biopsy marker mass is formed of particles of a bio-resorbable material having bubble cavities and having a particle size between about 200 microns and about 500 microns.

22 Claims, 3 Drawing Sheets

U.S. PATENT DOCUMENTS

| | | |
|---|---|---|
| 3,593,343 A | 7/1971 | Viggers |
| 3,757,781 A | 9/1973 | Smart |
| 3,818,894 A | 6/1974 | Wichterle et al. |
| 3,823,212 A | 7/1974 | Chvapil |
| 3,921,632 A | 11/1975 | Bardani |
| 4,005,699 A | 2/1977 | Bucalo |
| 4,007,732 A | 2/1977 | Kvavle et al. |
| 4,041,931 A | 8/1977 | Elliott et al. |
| 4,103,690 A | 8/1978 | Harris |
| 4,105,030 A | 8/1978 | Kercso |
| 4,172,449 A | 10/1979 | LeRoy et al. |
| 4,197,846 A | 4/1980 | Bucalo |
| 4,217,889 A | 8/1980 | Radovan et al. |
| 4,276,885 A | 7/1981 | Tickner et al. |
| 4,294,241 A | 10/1981 | Miyata |
| 4,298,998 A | 11/1981 | Naficy |
| 4,331,654 A | 5/1982 | Morris |
| 4,390,018 A | 6/1983 | Zukowski |
| 4,400,170 A | 8/1983 | McNaughton et al. |
| 4,401,124 A | 8/1983 | Guess et al. |
| 4,405,314 A | 9/1983 | Cope |
| 4,428,082 A | 1/1984 | Naficy |
| 4,438,253 A | 3/1984 | Casey et al. |
| 4,442,843 A | 4/1984 | Rasor et al. |
| 4,470,160 A | 9/1984 | Cavon |
| 4,487,209 A | 12/1984 | Mehl |
| 4,545,367 A | 10/1985 | Tucci |
| 4,549,560 A | 10/1985 | Andis |
| 4,582,061 A | 4/1986 | Fry |
| 4,582,640 A | 4/1986 | Smestad et al. |
| 4,588,395 A | 5/1986 | Lemelson |
| 4,597,753 A | 7/1986 | Turley |
| 4,647,480 A | 3/1987 | Ahmed |
| 4,655,226 A | 4/1987 | Lee |
| 4,661,103 A | 4/1987 | Harman |
| 4,682,606 A | 7/1987 | DeCaprio |
| 4,693,237 A | 9/1987 | Hoffman et al. |
| 4,740,208 A | 4/1988 | Cavon |
| 4,813,062 A | 3/1989 | Gilpatrick |
| 4,820,267 A | 4/1989 | Harman |
| 4,832,680 A | 5/1989 | Haber et al. |
| 4,832,686 A | 5/1989 | Anderson |
| 4,847,049 A | 7/1989 | Yamamoto |
| 4,863,470 A | 9/1989 | Carter |
| 4,870,966 A | 10/1989 | Dellon et al. |
| 4,874,376 A | 10/1989 | Hawkins, Jr. |
| 4,889,707 A | 12/1989 | Day et al. |
| 4,909,250 A | 3/1990 | Smith |
| 4,938,763 A | 7/1990 | Dunn et al. |
| 4,950,665 A | 8/1990 | Floyd |
| 4,963,150 A | 10/1990 | Brauman |
| 4,970,298 A | 11/1990 | Silver et al. |
| 4,989,608 A | 2/1991 | Ratner |
| 4,994,028 A | 2/1991 | Leonard et al. |
| 5,012,818 A | 5/1991 | Joishy |
| 5,059,197 A | 10/1991 | Urie et al. |
| 5,081,997 A | 1/1992 | Bosley, Jr. et al. |
| 5,120,802 A | 6/1992 | Mares et al. |
| 5,125,413 A | 6/1992 | Baran |
| 5,137,928 A | 8/1992 | Erbel et al. |
| 5,141,748 A | 8/1992 | Rizzo |
| 5,147,307 A | 9/1992 | Gluck |
| 5,147,631 A * | 9/1992 | Glajch et al. ............... 424/9.52 |
| 5,162,430 A | 11/1992 | Rhee et al. |
| 5,163,896 A | 11/1992 | Suthanthiran et al. |
| 5,195,540 A | 3/1993 | Shiber |
| 5,197,482 A | 3/1993 | Rank et al. |
| 5,199,441 A | 4/1993 | Hogle |
| 5,219,339 A | 6/1993 | Saito |
| 5,221,269 A | 6/1993 | Miller et al. |
| 5,231,615 A | 7/1993 | Endoh |
| 5,236,410 A | 8/1993 | Granov et al. |
| 5,242,759 A | 9/1993 | Hall |
| 5,250,026 A | 10/1993 | Ehrlich et al. |
| 5,271,961 A | 12/1993 | Mathiowitz et al. |
| 5,273,532 A | 12/1993 | Niezink et al. |
| 5,280,788 A | 1/1994 | Janes et al. |
| 5,281,197 A | 1/1994 | Arias et al. |
| 5,281,408 A | 1/1994 | Unger |
| 5,282,781 A | 2/1994 | Liprie |
| 5,284,479 A | 2/1994 | de Jong |
| 5,289,831 A | 3/1994 | Bosley |
| 5,320,613 A | 6/1994 | Houge et al. |
| 5,328,955 A | 7/1994 | Rhee et al. |
| 5,334,381 A | 8/1994 | Unger |
| 5,353,804 A | 10/1994 | Kornberg et al. |
| 5,354,623 A | 10/1994 | Hall |
| 5,366,756 A | 11/1994 | Chesterfield et al. |
| 5,368,030 A | 11/1994 | Zinreich |
| 5,388,588 A | 2/1995 | Nabai et al. |
| 5,394,875 A | 3/1995 | Lewis et al. |
| 5,395,319 A | 3/1995 | Hirsch et al. |
| 5,409,004 A | 4/1995 | Sloan |
| 5,417,708 A | 5/1995 | Hall et al. |
| 5,422,730 A | 6/1995 | Barlow et al. |
| 5,425,366 A | 6/1995 | Reinhardt et al. |
| 5,431,639 A | 7/1995 | Shaw |
| 5,433,204 A | 7/1995 | Olson |
| 5,449,560 A | 9/1995 | Antheunis et al. |
| 5,451,406 A | 9/1995 | Lawin et al. |
| 5,460,182 A | 10/1995 | Goodman et al. |
| 5,469,847 A | 11/1995 | Zinreich et al. |
| 5,475,052 A | 12/1995 | Rhee et al. |
| 5,490,521 A | 2/1996 | Davis et al. |
| 5,494,030 A | 2/1996 | Swartz et al. |
| 5,499,989 A | 3/1996 | LaBash |
| 5,507,807 A | 4/1996 | Shippert |
| 5,508,021 A | 4/1996 | Grinstaff et al. |
| 5,514,085 A | 5/1996 | Yoon |
| 5,522,896 A | 6/1996 | Prescott |
| 5,538,726 A | 7/1996 | Order |
| 5,542,915 A | 8/1996 | Edwards et al. |
| 5,549,560 A | 8/1996 | Van de Wijdeven |
| RE35,391 E | 12/1996 | Brauman |
| 5,580,568 A | 12/1996 | Greff et al. |
| 5,585,112 A | 12/1996 | Unger et al. |
| 5,611,352 A | 3/1997 | Kobren et al. |
| 5,626,611 A | 5/1997 | Liu et al. |
| 5,628,781 A | 5/1997 | Williams et al. |
| 5,629,008 A | 5/1997 | Lee |
| 5,636,255 A | 6/1997 | Ellis |
| 5,643,246 A | 7/1997 | Leeb et al. |
| 5,646,146 A | 7/1997 | Faarup et al. |
| 5,667,767 A | 9/1997 | Greff et al. |
| 5,673,841 A | 10/1997 | Schulze et al. |
| 5,676,146 A | 10/1997 | Scarborough |
| 5,676,925 A | 10/1997 | Klaveness et al. |
| 5,688,490 A | 11/1997 | Tournier et al. |
| 5,690,120 A | 11/1997 | Jacobsen et al. |
| 5,695,480 A | 12/1997 | Evans et al. |
| 5,702,128 A | 12/1997 | Maxim et al. |
| 5,702,716 A | 12/1997 | Dunn et al. |
| 5,747,060 A | 5/1998 | Sackler et al. |
| 5,762,903 A | 6/1998 | Park et al. |
| 5,769,086 A | 6/1998 | Ritchart et al. |
| 5,776,496 A * | 7/1998 | Violante et al. ............... 424/489 |
| 5,779,647 A | 7/1998 | Chau et al. |
| 5,782,764 A | 7/1998 | Werne |
| 5,782,775 A | 7/1998 | Milliman et al. |
| 5,795,308 A | 8/1998 | Russin |
| 5,799,099 A | 8/1998 | Wang et al. |
| 5,800,362 A | 9/1998 | Kobren et al. |
| 5,800,389 A | 9/1998 | Burney et al. |
| 5,800,445 A | 9/1998 | Ratcliff et al. |
| 5,800,541 A | 9/1998 | Rhee et al. |
| 5,817,022 A | 10/1998 | Vesely |
| 5,820,918 A | 10/1998 | Ronan et al. |
| 5,821,184 A | 10/1998 | Haines et al. |
| 5,823,198 A | 10/1998 | Jones et al. |
| 5,824,042 A | 10/1998 | Lombardi et al. |
| 5,824,081 A | 10/1998 | Knapp et al. |
| 5,830,178 A | 11/1998 | Jones et al. |
| 5,842,477 A | 12/1998 | Naughton et al. |
| 5,842,999 A | 12/1998 | Pruitt et al. |
| 5,845,646 A | 12/1998 | Lemelson |
| 5,846,220 A | 12/1998 | Elsberry |
| 5,851,508 A | 12/1998 | Greff et al. |

| Patent No. | Date | Inventor(s) |
|---|---|---|
| 5,853,366 A | 12/1998 | Dowlatshahi |
| 5,865,806 A | 2/1999 | Howell |
| 5,869,080 A | 2/1999 | McGregor et al. |
| 5,871,501 A | 2/1999 | Leschinsky et al. |
| 5,876,340 A | 3/1999 | Tu et al. |
| 5,879,357 A | 3/1999 | Heaton et al. |
| 5,891,558 A | 4/1999 | Bell et al. |
| 5,897,507 A | 4/1999 | Kortenbach et al. |
| 5,902,310 A | 5/1999 | Foerster et al. |
| 5,911,705 A | 6/1999 | Howell |
| 5,916,164 A | 6/1999 | Fitzpatrick et al. |
| 5,921,933 A * | 7/1999 | Sarkis et al. .................. 600/459 |
| 5,922,024 A | 7/1999 | Janzen et al. |
| 5,928,626 A | 7/1999 | Klaveness et al. |
| 5,928,773 A | 7/1999 | Andersen |
| 5,941,439 A | 8/1999 | Kammerer et al. |
| 5,941,890 A | 8/1999 | Voegele et al. |
| 5,942,209 A | 8/1999 | Leavitt et al. |
| 5,948,425 A | 9/1999 | Janzen et al. |
| 5,954,670 A | 9/1999 | Baker |
| 5,972,817 A | 10/1999 | Haines et al. |
| 5,989,265 A | 11/1999 | Bouquet De La Joliniere et al. |
| 6,015,541 A | 1/2000 | Greff et al. |
| 6,030,333 A | 2/2000 | Sioshansi et al. |
| 6,053,925 A | 4/2000 | Barnhart |
| 6,056,700 A | 5/2000 | Burney et al. |
| 6,066,122 A | 5/2000 | Fisher |
| 6,066,325 A | 5/2000 | Wallace et al. |
| 6,071,301 A | 6/2000 | Cragg et al. |
| 6,071,310 A | 6/2000 | Picha et al. |
| 6,071,496 A | 6/2000 | Stein et al. |
| 6,096,065 A | 8/2000 | Crowley |
| 6,096,070 A | 8/2000 | Ragheb et al. |
| 6,106,473 A | 8/2000 | Violante et al. |
| 6,117,108 A | 9/2000 | Woehr et al. |
| 6,120,536 A | 9/2000 | Ding et al. |
| 6,142,955 A | 11/2000 | Farascioni et al. |
| 6,159,445 A | 12/2000 | Klaveness et al. |
| 6,161,034 A | 12/2000 | Burbank et al. |
| 6,162,192 A | 12/2000 | Cragg et al. |
| 6,173,715 B1 | 1/2001 | Sinanan et al. |
| 6,174,330 B1 | 1/2001 | Stinson |
| 6,177,062 B1 | 1/2001 | Stein et al. |
| 6,181,960 B1 | 1/2001 | Jensen et al. |
| 6,183,497 B1 | 2/2001 | Sing et al. |
| 6,190,350 B1 | 2/2001 | Davis et al. |
| 6,200,258 B1 | 3/2001 | Slater et al. |
| 6,203,524 B1 | 3/2001 | Burney et al. |
| 6,203,568 B1 | 3/2001 | Lombardi et al. |
| 6,213,957 B1 | 4/2001 | Milliman et al. |
| 6,214,045 B1 | 4/2001 | Corbitt, Jr. et al. |
| 6,214,315 B1 | 4/2001 | Greff et al. |
| 6,220,248 B1 | 4/2001 | Voegele et al. |
| 6,224,630 B1 | 5/2001 | Bao et al. |
| 6,228,049 B1 | 5/2001 | Schroeder et al. |
| 6,228,055 B1 | 5/2001 | Foerster et al. |
| 6,231,615 B1 | 5/2001 | Preissman |
| 6,234,177 B1 | 5/2001 | Barsch |
| 6,241,687 B1 | 6/2001 | Voegele et al. |
| 6,241,734 B1 | 6/2001 | Scribner et al. |
| 6,251,418 B1 | 6/2001 | Ahern et al. |
| 6,261,243 B1 | 7/2001 | Burney et al. |
| 6,261,302 B1 | 7/2001 | Voegele et al. |
| 6,264,917 B1 * | 7/2001 | Klaveness et al. ............ 424/9.52 |
| 6,270,464 B1 | 8/2001 | Fulton, III et al. |
| 6,270,472 B1 | 8/2001 | Antaki et al. |
| 6,287,278 B1 | 9/2001 | Woehr et al. |
| 6,287,332 B1 | 9/2001 | Bolz et al. |
| 6,289,229 B1 | 9/2001 | Crowley |
| 6,312,429 B1 | 11/2001 | Burbank et al. |
| 6,316,522 B1 | 11/2001 | Loomis et al. |
| 6,335,029 B1 | 1/2002 | Kamath et al. |
| 6,336,904 B1 | 1/2002 | Nikolchev |
| 6,340,367 B1 | 1/2002 | Stinson et al. |
| 6,343,227 B1 | 1/2002 | Crowley |
| 6,347,240 B1 | 2/2002 | Foley et al. |
| 6,347,241 B2 | 2/2002 | Burbank et al. |
| 6,350,244 B1 | 2/2002 | Fisher |
| 6,350,274 B1 | 2/2002 | Li |
| 6,354,989 B1 | 3/2002 | Nudeshima |
| 6,356,112 B1 | 3/2002 | Tran et al. |
| 6,356,782 B1 | 3/2002 | Sirimanne et al. |
| 6,358,217 B1 | 3/2002 | Bourassa |
| 6,363,940 B1 | 4/2002 | Krag |
| 6,371,904 B1 | 4/2002 | Sirimanne et al. |
| 6,394,965 B1 | 5/2002 | Klein |
| 6,403,758 B1 | 6/2002 | Loomis |
| 6,405,733 B1 | 6/2002 | Fogarty et al. |
| 6,409,742 B1 | 6/2002 | Fulton, III et al. |
| 6,424,857 B1 | 7/2002 | Henrichs et al. |
| 6,425,903 B1 | 7/2002 | Voegele |
| 6,427,081 B1 | 7/2002 | Burbank et al. |
| 6,450,937 B1 | 9/2002 | Mercereau et al. |
| 6,450,938 B1 | 9/2002 | Miller |
| 6,471,700 B1 | 10/2002 | Burbank et al. |
| 6,506,156 B1 | 1/2003 | Jones et al. |
| 6,511,468 B1 | 1/2003 | Cragg et al. |
| 6,537,193 B1 | 3/2003 | Lennox |
| 6,540,981 B2 | 4/2003 | Klaveness et al. |
| 6,544,185 B2 | 4/2003 | Montegrande |
| 6,551,253 B2 | 4/2003 | Worm et al. |
| 6,554,760 B2 | 4/2003 | Lamoureux et al. |
| 6,562,317 B2 | 5/2003 | Greff et al. |
| 6,564,806 B1 | 5/2003 | Fogarty et al. |
| 6,565,551 B1 | 5/2003 | Jones et al. |
| 6,567,689 B2 | 5/2003 | Burbank et al. |
| 6,575,888 B2 | 6/2003 | Zamora et al. |
| 6,575,991 B1 | 6/2003 | Chesbrough et al. |
| 6,605,047 B2 | 8/2003 | Zarins et al. |
| 6,610,026 B2 | 8/2003 | Cragg et al. |
| 6,613,002 B1 | 9/2003 | Clark et al. |
| 6,616,630 B1 | 9/2003 | Woehr et al. |
| 6,626,850 B1 | 9/2003 | Kupec et al. |
| 6,628,982 B1 | 9/2003 | Thomas et al. |
| 6,636,758 B2 | 10/2003 | Sanchez et al. |
| 6,638,234 B2 | 10/2003 | Burbank et al. |
| 6,638,308 B2 | 10/2003 | Corbitt, Jr. et al. |
| 6,652,442 B2 | 11/2003 | Gatto |
| 6,656,192 B2 | 12/2003 | Espositio et al. |
| 6,662,041 B2 | 12/2003 | Burbank et al. |
| 6,699,205 B2 | 3/2004 | Fulton, III et al. |
| 6,712,774 B2 | 3/2004 | Voegele et al. |
| 6,712,836 B1 | 3/2004 | Berg et al. |
| 6,716,444 B1 | 4/2004 | Castro et al. |
| 6,725,083 B1 | 4/2004 | Burbank et al. |
| 6,730,042 B2 | 5/2004 | Fulton et al. |
| 6,730,044 B2 | 5/2004 | Stephens et al. |
| 6,746,661 B2 | 6/2004 | Kaplan |
| 6,746,773 B2 | 6/2004 | Llanos et al. |
| 6,752,154 B2 | 6/2004 | Fogarty et al. |
| 6,766,186 B1 | 7/2004 | Hoyns et al. |
| 6,774,278 B1 | 8/2004 | Ragheb et al. |
| 6,780,179 B2 | 8/2004 | Lee et al. |
| 6,824,507 B2 | 11/2004 | Miller |
| 6,824,527 B2 | 11/2004 | Gollobin |
| 6,846,320 B2 | 1/2005 | Ashby et al. |
| 6,862,470 B2 | 3/2005 | Burbank et al. |
| 6,863,685 B2 | 3/2005 | Davila et al. |
| 6,899,731 B2 | 5/2005 | Li et al. |
| 6,918,927 B2 | 7/2005 | Bates et al. |
| 6,936,014 B2 | 8/2005 | Vetter et al. |
| 6,939,318 B2 | 9/2005 | Stenzel |
| 6,945,973 B2 | 9/2005 | Bray |
| 6,951,564 B2 | 10/2005 | Espositio et al. |
| 6,992,233 B2 | 1/2006 | Drake et al. |
| 6,994,712 B1 | 2/2006 | Fisher et al. |
| 7,001,341 B2 | 2/2006 | Gellman et al. |
| 7,008,382 B2 | 3/2006 | Adams et al. |
| 7,014,610 B2 | 3/2006 | Koulik |
| 7,025,765 B2 | 4/2006 | Balbierz et al. |
| 7,044,957 B2 | 5/2006 | Foerster et al. |
| 7,083,576 B2 | 8/2006 | Zarins et al. |
| 7,125,397 B2 | 10/2006 | Woehr et al. |
| 7,172,549 B2 | 2/2007 | Slater et al. |
| 7,214,211 B2 | 5/2007 | Woehr et al. |
| 7,229,417 B2 | 6/2007 | Foerster et al. |
| 7,236,816 B2 | 6/2007 | Kumar et al. |
| 7,264,613 B2 | 9/2007 | Woehr et al. |

| | | |
|---|---|---|
| 7,294,118 B2 | 11/2007 | Saulenas et al. |
| 7,297,725 B2 | 11/2007 | Winterton et al. |
| 7,329,402 B2 | 2/2008 | Unger et al. |
| 7,416,533 B2 | 8/2008 | Gellman et al. |
| 7,449,000 B2 | 11/2008 | Adams et al. |
| 7,527,610 B2 | 5/2009 | Erickson |
| 7,569,065 B2 | 8/2009 | Chesbrough et al. |
| 7,637,948 B2 | 12/2009 | Corbitt, Jr. |
| 2001/0003791 A1 | 6/2001 | Burbank et al. |
| 2001/0006616 A1 | 7/2001 | Leavitt et al. |
| 2001/0033867 A1 | 10/2001 | Ahern et al. |
| 2001/0034528 A1 | 10/2001 | Foerster et al. |
| 2001/0049481 A1 | 12/2001 | Fulton, III et al. |
| 2002/0004060 A1 | 1/2002 | Heublein et al. |
| 2002/0016625 A1 | 2/2002 | Falotico et al. |
| 2002/0022883 A1 | 2/2002 | Burg |
| 2002/0026201 A1 | 2/2002 | Foerster et al. |
| 2002/0035324 A1 | 3/2002 | Sirimanne et al. |
| 2002/0038087 A1 | 3/2002 | Burbank et al. |
| 2002/0045842 A1 | 4/2002 | Van Bladel et al. |
| 2002/0052572 A1 | 5/2002 | Franco et al. |
| 2002/0055731 A1 | 5/2002 | Atala et al. |
| 2002/0058868 A1 | 5/2002 | Hoshino et al. |
| 2002/0058882 A1 | 5/2002 | Fulton, III et al. |
| 2002/0077687 A1 | 6/2002 | Ahn |
| 2002/0082519 A1 | 6/2002 | Miller et al. |
| 2002/0082682 A1 | 6/2002 | Barclay et al. |
| 2002/0082683 A1 | 6/2002 | Stinson et al. |
| 2002/0095204 A1 | 7/2002 | Thompson et al. |
| 2002/0095205 A1 | 7/2002 | Edwin et al. |
| 2002/0107437 A1 | 8/2002 | Sirimanne et al. |
| 2002/0133148 A1 | 9/2002 | Daniel et al. |
| 2002/0143359 A1 | 10/2002 | Fulton, III et al. |
| 2002/0165608 A1 | 11/2002 | Llanos et al. |
| 2002/0188196 A1 | 12/2002 | Burbank et al. |
| 2002/0193815 A1 | 12/2002 | Foerster et al. |
| 2002/0193867 A1 | 12/2002 | Gladdish, Jr. et al. |
| 2003/0036803 A1 | 2/2003 | McGhan |
| 2003/0051735 A1 | 3/2003 | Pavcnik et al. |
| 2003/0116806 A1 | 6/2003 | Kato |
| 2003/0165478 A1 | 9/2003 | Sokoll |
| 2003/0191355 A1 | 10/2003 | Ferguson |
| 2003/0199887 A1 | 10/2003 | Ferrera et al. |
| 2003/0225420 A1 | 12/2003 | Wardle |
| 2003/0233101 A1 | 12/2003 | Lubock et al. |
| 2003/0236573 A1 | 12/2003 | Evans et al. |
| 2004/0001841 A1 | 1/2004 | Nagavarapu et al. |
| 2004/0002650 A1 | 1/2004 | Mandrusov et al. |
| 2004/0016195 A1 | 1/2004 | Archuleta |
| 2004/0024304 A1 | 2/2004 | Foerster et al. |
| 2004/0059341 A1 | 3/2004 | Gellman et al. |
| 2004/0073107 A1 | 4/2004 | Sioshansi et al. |
| 2004/0073284 A1 | 4/2004 | Bates et al. |
| 2004/0097981 A1 | 5/2004 | Selis |
| 2004/0101479 A1 | 5/2004 | Burbank et al. |
| 2004/0101548 A1 | 5/2004 | Pendharkar |
| 2004/0106891 A1 | 6/2004 | Langan et al. |
| 2004/0116802 A1 | 6/2004 | Jessop et al. |
| 2004/0116806 A1 | 6/2004 | Burbank et al. |
| 2004/0124105 A1 | 7/2004 | Seiler et al. |
| 2004/0127765 A1 | 7/2004 | Seiler et al. |
| 2004/0162574 A1 | 8/2004 | Viola |
| 2004/0167619 A1 | 8/2004 | Case et al. |
| 2004/0193044 A1 | 9/2004 | Burbank et al. |
| 2004/0204660 A1 | 10/2004 | Fulton et al. |
| 2004/0210208 A1 | 10/2004 | Paul et al. |
| 2004/0213756 A1 | 10/2004 | Michal et al. |
| 2004/0236211 A1 | 11/2004 | Burbank et al. |
| 2004/0236212 A1 | 11/2004 | Jones et al. |
| 2004/0236213 A1 | 11/2004 | Jones et al. |
| 2005/0020916 A1 | 1/2005 | MacFarlane et al. |
| 2005/0033157 A1 | 2/2005 | Klien et al. |
| 2005/0033195 A1 | 2/2005 | Fulton et al. |
| 2005/0036946 A1 | 2/2005 | Pathak et al. |
| 2005/0045192 A1 | 3/2005 | Fulton et al. |
| 2005/0059887 A1 | 3/2005 | Mostafavi et al. |
| 2005/0059888 A1 | 3/2005 | Sirimanne et al. |
| 2005/0063908 A1 | 3/2005 | Burbank et al. |
| 2005/0065354 A1 | 3/2005 | Roberts |
| 2005/0065453 A1 | 3/2005 | Shabaz et al. |
| 2005/0080337 A1 | 4/2005 | Sirimanne et al. |
| 2005/0080339 A1 | 4/2005 | Sirimanne et al. |
| 2005/0085724 A1 | 4/2005 | Sirimanne et al. |
| 2005/0100580 A1 | 5/2005 | Osborne et al. |
| 2005/0113659 A1 | 5/2005 | Pothier et al. |
| 2005/0119562 A1 | 6/2005 | Jones et al. |
| 2005/0143650 A1 | 6/2005 | Winkel |
| 2005/0165305 A1 | 7/2005 | Foerster et al. |
| 2005/0175657 A1 | 8/2005 | Hunter et al. |
| 2005/0181007 A1 | 8/2005 | Hunter et al. |
| 2005/0208122 A1 | 9/2005 | Allen et al. |
| 2005/0234336 A1 | 10/2005 | Beckman et al. |
| 2005/0268922 A1 | 12/2005 | Conrad et al. |
| 2005/0273002 A1 | 12/2005 | Goosen et al. |
| 2005/0277871 A1 | 12/2005 | Selis |
| 2006/0004440 A1 | 1/2006 | Stinson |
| 2006/0009800 A1 | 1/2006 | Christianson et al. |
| 2006/0036158 A1 | 2/2006 | Field et al. |
| 2006/0036159 A1 | 2/2006 | Sirimanne et al. |
| 2006/0036165 A1 | 2/2006 | Burbank et al. |
| 2006/0074443 A1 | 4/2006 | Foerster et al. |
| 2006/0079770 A1 | 4/2006 | Sirimanne et al. |
| 2006/0079805 A1 | 4/2006 | Miller et al. |
| 2006/0079829 A1 | 4/2006 | Fulton et al. |
| 2006/0079888 A1 | 4/2006 | Mulier et al. |
| 2006/0122503 A1 | 6/2006 | Burbank et al. |
| 2006/0155190 A1 | 7/2006 | Burbank et al. |
| 2006/0173296 A1 | 8/2006 | Miller et al. |
| 2006/0177379 A1 | 8/2006 | Asgari |
| 2006/0217635 A1 | 9/2006 | McCombs et al. |
| 2006/0235298 A1 | 10/2006 | Kotmel et al. |
| 2006/0241385 A1 | 10/2006 | Dietz |
| 2006/0292690 A1 | 12/2006 | Liu et al. |
| 2007/0021642 A1 | 1/2007 | Lamoureux et al. |
| 2007/0057794 A1 | 3/2007 | Gisselberg et al. |
| 2007/0083132 A1 | 4/2007 | Sharrow |
| 2007/0106152 A1 | 5/2007 | Kantrowitz et al. |
| 2007/0135711 A1 | 6/2007 | Chernomorsky et al. |
| 2007/0142725 A1 | 6/2007 | Hardin et al. |
| 2007/0167736 A1 | 7/2007 | Dietz et al. |
| 2007/0167749 A1 | 7/2007 | Yarnall et al. |
| 2007/0239118 A1 | 10/2007 | Ono et al. |
| 2007/0287933 A1 | 12/2007 | Phan et al. |
| 2008/0097199 A1 | 4/2008 | Mullen |
| 2008/0188768 A1 | 8/2008 | Zarins et al. |
| 2008/0269638 A1 | 10/2008 | Cooke et al. |
| 2009/0000629 A1 | 1/2009 | Hornscheidt et al. |
| 2009/0024225 A1 | 1/2009 | Stubbs |
| 2009/0069713 A1 | 3/2009 | Adams et al. |
| 2009/0076484 A1 | 3/2009 | Fukaya |
| 2009/0131825 A1 | 5/2009 | Burbank et al. |

FOREIGN PATENT DOCUMENTS

| | | |
|---|---|---|
| EP | 146699 A1 | 7/1985 |
| EP | 0255123 A2 | 3/1988 |
| EP | 0292936 A2 | 11/1988 |
| EP | 0386936 A1 | 12/1990 |
| EP | 0458745 A1 | 11/1991 |
| EP | 0475077 A2 | 3/1992 |
| EP | 0481685 A1 | 4/1992 |
| EP | 0552924 A1 | 7/1993 |
| EP | 0769281 A2 | 4/1997 |
| EP | 1114618 A2 | 1/2001 |
| EP | 1163888 A1 | 12/2001 |
| EP | 1216721 A2 | 6/2002 |
| EP | 1281416 A2 | 6/2002 |
| EP | 1364628 A1 | 11/2003 |
| EP | 1493451 A1 | 6/2004 |
| EP | 1767167 A2 | 3/2007 |
| FR | 2646674 A3 | 11/1990 |
| GB | 708148 A | 4/1954 |
| JP | 2131757 A | 5/1990 |
| WO | 8906978 A1 | 8/1989 |
| WO | 9112823 A1 | 9/1991 |
| WO | 9314712 A1 | 8/1993 |
| WO | 9317671 A1 | 9/1993 |
| WO | 9317718 A1 | 9/1993 |
| WO | 9416647 A1 | 8/1994 |

| | | | |
|---|---|---|---|
| WO | 9507057 A1 | 3/1995 |
| WO | 9608208 A1 | 3/1996 |
| WO | 9806346 A1 | 2/1998 |
| WO | 9908607 A1 | 2/1999 |
| WO | 9930764 A1 | 6/1999 |
| WO | 9935966 A1 | 7/1999 |
| WO | 9951143 A1 | 10/1999 |
| WO | 0023124 A1 | 4/2000 |
| WO | 0024332 A1 | 5/2000 |
| WO | 0028554 A1 | 5/2000 |
| WO | 0038579 A2 | 7/2000 |
| WO | 0054689 A1 | 9/2000 |
| WO | 0108578 A1 | 2/2001 |
| WO | 0170114 A1 | 9/2001 |
| WO | 0207786 A2 | 1/2002 |
| WO | 03000308 A1 | 1/2003 |
| WO | 2004045444 A2 | 6/2004 |
| WO | 2004105626 A2 | 12/2004 |
| WO | 2005013832 A1 | 2/2005 |
| WO | 2005039446 A1 | 5/2005 |
| WO | 2005089664 A1 | 9/2005 |
| WO | 2006056739 A2 | 6/2006 |
| WO | 2006097331 A2 | 9/2006 |
| WO | 2006105353 A2 | 10/2006 |
| WO | 2007069105 A2 | 6/2007 |
| WO | 2008077081 A2 | 6/2008 |

OTHER PUBLICATIONS

Shiga et al., Preparation of Poly(D, L-lactide) and Copoly(lactide-glycolide) Microspheres of Uniform Size, J. Pharm. Pharmacol. 1996 48:891-895.

Eiselt, P. et al, "Development of Technologies Aiding Large—Tissue Engineering", Biotechnol, Prog., vol. 14, No. 1, pp. 134-140, 1998.

Schindlbeck, N.E., et al., "Measurement of Colon Transit Time" ["Messung der Kolontransitzeit"], J. of Gastroenterology, No. 28, pp. 399-404, 1990.

Fucci, V., et al., "Large Bowel Transit Times Using Radiopaque Markers in Normal Cats", J. of Am. Animal Hospital Assn., Nov.-Dec. 1995 31 (6) 473-477.

Press release for Biopsys Ethicon Endo-Surgery (Europe) GmbH; The Mammotome Vacuum Biopsy System. From: http://www.medicine-news.com/articles/devices/mammotome.html. 3 pages.

Johnson & Johnson: Breast Biopsy (minimally invasive): Surgical Technique: Steps in the Mamotome Surgical Procedure. From http://www.jnjgateway.com. 3 pages.

Johnson & Johnson: New Minimally Invasive Breast Biopsy Device Receives Marketing Clearance in Canada; Aug. 6, 1999. From http://www.jnjgateway.com. 4 pages.

Johnson & Johnson: Mammotome Hand Held Receives FDA Marketing Clearance for Minimally Invasive Breast Biopises; Sep. 1, 1999. From From http://www.jnjgateway.com. 5 pages.

Johnson & Johnson: The Mammotome Breast Biopsy System. From: http://www.breastcareinfo.com/aboutm.htm. 6 pages.

Cook Incorporated: Emoblization and Occlusion. From: www.cookgroup.com 6 pages.

Liberman, Laura, et al. Percutaneous Removal of Malignant Mammographic Lesions at Stereotactic Vacuum-assisted Biopsy. From: The Departments of Radiology, Pathology, and Surgery. Memorial Sloan-Kettering Cancer Center. From the 1997 RSNA scientific assembly. vol. 206, No. 3. pp. 711-715.

Meuris, Bart, "Calcification of Aortic Wall Tissue in Prosthetic Heart Valves: Initiation, Influencing Factors and Strategies Towards Prevention", Thesis, 2007, pp. 21-36, Leuven University Press; Leuven, Belgium.

* cited by examiner

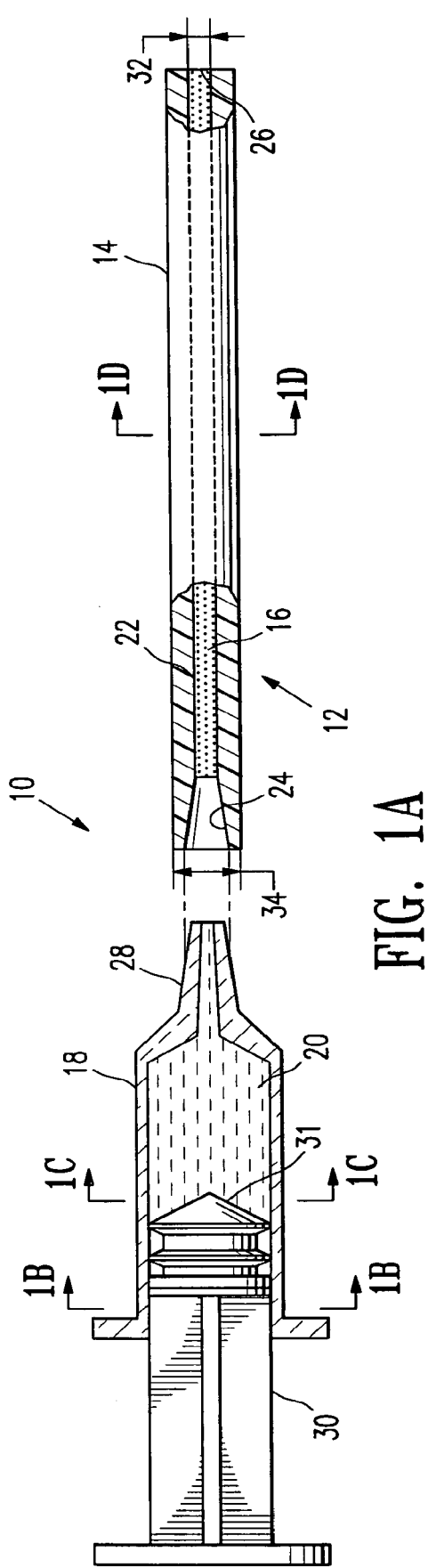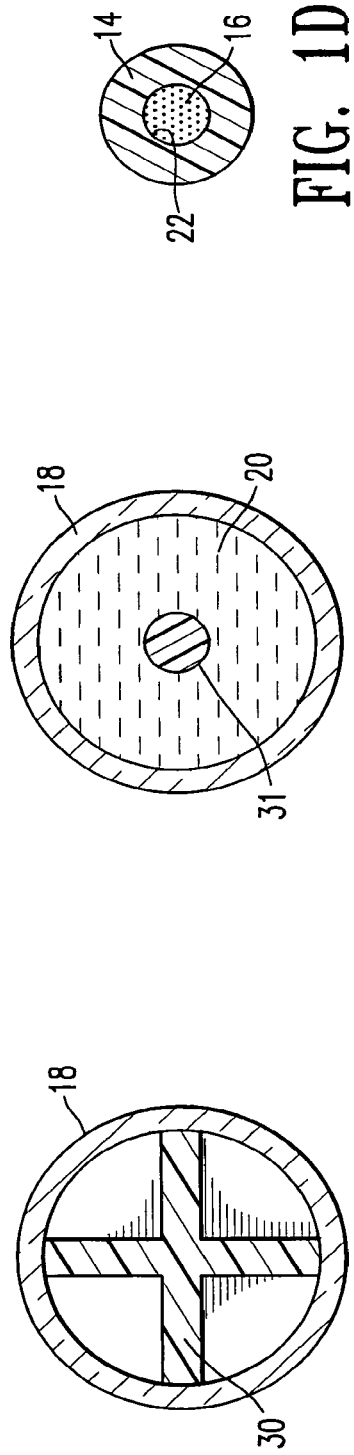

CAVITY-FILLING BIOPSY SITE MARKERS

CROSS-REFERENCE TO RELATED APPLICATIONS

This application is a continuation of application Ser. No. 10/990,327, filed Nov. 16, 2004, now U.S. Pat. No. 7,792,569, which is a continuation of application Ser. No. 10/124,757, filed Apr. 16, 2002, now U.S. Pat. No. 6,862,470, which is a continuation-in-part of application Ser. No. 09/717,909, filed Nov. 20, 2000, now U.S. Pat. No. 6,725,083, which is a continuation-in-part of application Ser. No. 09/343,975, filed Jun. 30, 1999, now U.S. Pat. No. 6,347,241, which is a continuation-in-part of application Ser. No. 09/241,936, filed Feb. 2, 1999, now U.S. Pat. No. 6,161,034, which are all hereby incorporated by reference herein in their entireties and from all of which priority is hereby claimed under 35 U.S.C. §119(e) and §120.

FIELD OF THE INVENTION

This invention relates generally to the field of acquisition of tissue from a patient, as occurs in a biopsy procedure, in particular to the marking of the site within a body from which a biopsy has been taken.

BACKGROUND OF THE INVENTION

In diagnosing and treating certain medical conditions, it is often desirable to perform a biopsy, in which a specimen or sample of tissue is removed for pathological examination, tests and analysis. As is known, obtaining a tissue sample by biopsy and the subsequent examination are typically employed in the diagnosis of cancers and other malignant tumors, or to confirm that a suspected lesion or tumor is not malignant. The information obtained from these diagnostic tests and/or examinations is frequently used to devise a plan for the appropriate surgical procedure or other course of treatment. For example, breast biopsies may be taken where a suspicious lump or swelling is noticed in a breast. Examination of tissue samples taken by biopsy is of particular significance in the diagnosis and treatment of breast cancer. In the ensuing discussion, the biopsy and treatment site described will generally be the human breast, although the invention is suitable for marking biopsy sites in other parts of the human and other mammalian body as well.

After the biopsy sample is taken, it may take several days or weeks before the results of the examination of the sample are obtained, and still longer before an appropriate treatment decision is reached. If the decision involves surgery it is clearly important for the surgeon to find the location in the breast from where the tumor tissue has been taken in the biopsy procedure, so that the entire tumor and possibly surrounding healthy tissue can be removed.

However, radiographically imageable tissue features, originally detected in a mammogram, may be removed, altered or obscured by the biopsy procedure. In order for the surgeon or radiation oncologist to direct surgical or radiation treatment to the precise location of the breast lesion several days or weeks after the biopsy procedure was performed, it is desirable that a biopsy site marker be placed in or on the patient's body to serve as a landmark for subsequent location of the lesion.

Various types of biopsy site markers have been described, including visible markers applied externally to the patient's skin, radiographically (X-ray)-detectable tissue markers such as clips and staples, and ultrasound-detectable markers, have also been described. X-ray-detectable marker wires may be inserted through a biopsy needle, leading from the surface of the patient's body to the biopsy site. Some markers may be biodegradable.

However, due to the consistency of breast tissue and the fact that these biopsy site markers are typically introduced while the breast is still compressed between the mammography plates, prior art biopsy markers do not always remain at the specific biopsy location after the breast has been decompressed and removed from the mammography apparatus, and may suffer from additional disadvantages as well. In order to locate an X-ray-detectable marker left at a biopsy site, an additional mammography is generally required at the time of follow up treatment or surgery. In addition, once the biopsy site is located using mammography, the site must usually be marked again with a location wire that is visible to provide guidance to the clinician performing the treatment or surgery. However, as the patient is removed from the mammography apparatus, or otherwise transported, the position of the location wire can change or shift before the treatment or surgery is performed, which may result in treatments being misdirected to undesired locations. Furthermore, at least some prior art biopsy site markers can remain present at the site of implantation for an indefinite period of time and, if not surgically removed, may obscure or otherwise interfere with any subsequent mammography or imaging studies.

As an alternative or adjunct to radiographic imaging, ultrasonic imaging and visualization techniques (abbreviated as "USI") can be used to image the tissue of interest at the site of interest during a surgical or biopsy procedure or follow-up procedure. USI is capable of providing precise location and imaging of suspicious tissue, surrounding tissue and biopsy instruments within the patient's body during a procedure. Such imaging facilitates accurate and controllable removal or sampling of the suspicious tissue so as to minimize trauma to surrounding healthy tissue.

For example, during a breast biopsy procedure, the biopsy device is often imaged with USI while the device is being inserted into the patient's breast and activated to remove a sample of suspicious breast tissue. As USI is often used to image tissue during follow-up treatment, it may be desirable to have a marker, similar to the radiographic markers discussed above, which can be placed in a patient's body at the site of a surgical procedure and which are detectable using USI. However, radiopaque markers may not be detectable with USI. A marker that is detectable with USI enables a follow-up procedure to be performed without the need for traditional radiographic mammography imaging which, as discussed above, can be subject to inaccuracies as a result of shifting of the location wire as well as being tedious and uncomfortable for the patient.

Thus, there is need in the art for biopsy site markers that are deliverable into the cavity created by removal of the biopsy specimen and not into tissue that is located outside of that biopsy cavity, and which will not migrate from the biopsy cavity even when the breast tissue is moved, manipulated or decompressed. Moreover, such desired markers should remain detectable at the biopsy site (i.e., within the biopsy cavity for a desired time period); should not interfere with imaging of the biopsy site and adjacent tissues at a later time; and should be readily distinguishable in the various imaging procedures from lines of calcifications which frequently are signs for a developing malignancy.

SUMMARY OF THE INVENTION

The invention is directed to materials, devices, and methods for marking intracorporeal locations such as biopsy sites for a limited time. The marking material comprises an ultrasound-detectable bio-resorbable finely-divided particulate material (such as a powder), in which many of the particles have internal cavities. Such particulate materials or powders may be composed of particles having sizes typically less than about 2000 microns, and typically between about 20 microns and about 2000 microns, preferably between about 20 microns and about 800 microns, more preferably between about 300 microns and about 500 microns.

The ultrasound-detectable bio-resorbable particulate materials may include any bio-resorbable particulate material having cavities which facilitate USI. For example, the ultrasound-detectable bio-resorbable particulate materials include particles having cavities with dimensions typically between about 10 microns and about 500 microns, preferably about 20 microns to about 200 microns. The particulate materials may also contain binding agents. Typically, a mass of the bio-resorbable particulate material is delivered to an intracorporeal location, such as a biopsy site within a patient. The mass of particulate material remains situated and detectable at the biopsy site during a limited time until it is resorbed by tissue near the biopsy site. Delivery devices having features of the invention are configured to contain the deliverable mass of particles, to fit within a cannula, and to engage with a syringe. Systems for temporarily marking an intracorporeal site may include a tube containing an ultrasound-detectable bio-resorbable powder, and a syringe containing a biocompatible fluid for biopsy site marking. The tube may be configured to fit within a cannula, such as a Mammotome® or SenoCor 360™ biopsy cannula or a coaxial needle guide.

The biopsy site marker materials include powders and powder slurries which can be delivered into a biopsy site cavity. Thus, much or all of the biopsy cavity may be filled with an ultrasound-detectable marker material, creating an ultrasound-detectable marker that can be as large as the biopsy sample that was removed from the patient's body. In addition, this allows the ultrasound detection and definition of the boundaries of the biopsy cavity. The needle track leading to the biopsy cavity may be filled as well if desired. Marker materials embodying features of the invention may be deposited at an intracorporeal location along with other agents, including anesthetic agents, hemostatic agents, pigments, dyes, materials detectable by magnetic resonance imaging (MRI), inert materials, and other compounds. For example, marker materials embodying features of the invention may include radiopaque materials as well as ultrasound-detectable materials. Such radiopaque material can serve to provide temporary or permanent radiographic marking of the location. Upon deposition at a biopsy site within a patient, materials embodying features of the invention may set up or gel to form flexible or relatively rigid solid masses.

The ultrasound-detectable biopsy site markers of the present invention provide several advantages. A biopsy cavity with a marker material having features of the present invention provides a large USI-bright mass, making it much easier, for example, to distinguish the ultrasound signal of the marker from signals arising naturally from within a breast. The marker materials produce bright ultrasound echo signals from one portion of the filled region, which contrasts with the dark ultrasound shadow region immediately behind the bright ultrasound echo region. The strength of the reflected signal, and the contrast with the shadow region, make the marked site readily detectable. Such ready detectability allows, for example, lesser-experienced physicians to perform the identification by USI and the subsequent surgical resection without the need for an interventional radiologist to identify and mark the biopsy cavity. These and other advantages will be further described in the following detailed description of embodiments of the invention.

BRIEF DESCRIPTION OF THE DRAWINGS

FIG. 1A is an elevational view, partially in section, of a system embodying features of the invention.

FIG. 1B is a transverse cross-sectional view of a syringe of a system embodying features of the invention, taken along line 1B-1B shown in FIG. 1A.

FIG. 1C is a transverse cross-sectional view of a syringe of a system embodying features of the invention, taken along line 1C-1C shown in FIG. 1A.

FIG. 1D is a transverse cross-sectional view of a tube of a system embodying features of the invention, taken along line 1D-1D shown in FIG. 1A.

DETAILED DESCRIPTION OF THE PREFERRED EMBODIMENTS

Figure 2B:
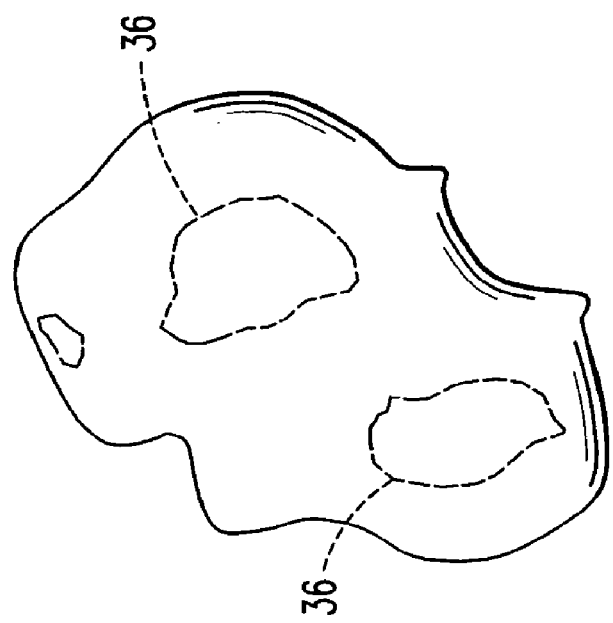
FIG. 2B is a perspective view of a particle of an ultrasound-detectable bio-resorbable marker material embodying features of the invention, having enclosed bubble cavities indicated with dotted lines.

FIGS. 1A-1D illustrate elements of a system 10 embodying features of the invention, including a delivery tube 14 containing a quantity of an ultrasound-detectable bio-resorbable particulate material 16 having features of the invention, and a syringe 18. The system 10 (including tube 14, material 16 and syringe 18) includes an assembly 12 (which includes a delivery tube 14 containing a quantity of ultrasound-detectable bio-resorbable particulate material 16). In FIG. 1A, an assembly 12 is shown oriented to engage with a syringe 18 containing a bio-compatible fluid 20 such as sterile saline. Delivery tube 14 has a bore 22 extending from a receptacle 24 through to an outlet 26. The quantity of ultrasound-detectable bio-resorbable particulate material 16 is contained within bore 22. Receptacle 24 is configured to receive tip 28 of syringe 18 effective to form a fluid-tight engagement. As illustrated in FIG. 1, tip 28 is a luer-lock tip; it will be understood that other tips and locking arrangements may be used in other embodiments of the invention. This fluid-tight engagement is able to contain fluid 20 and prevent its leakage out of receptacle 24 when plunger 30 is depressed, moving gasket 31 forward and forcing fluid 20 to flow out of syringe 18 and into bore 22. In bore 22 the fluid 20 mixes with particulate material 16 and carries particulate material 16 out of tube outlet 26. Bore inner diameter 32 is sufficiently large to allow ready outflow of fluid 20 and particulate material 16. Delivery tube outer diameter 34 is configured to be small enough that delivery tube 14 may be readily inserted into a cannula, such as a biopsy guide cannula.

A delivery tube 14 may have indicia, such as lines or dots spaced at regular intervals along a length of the tube to indicate the tube's position within a cannula. A delivery tube 14 may also be configured with a stop, such as a bump, peg, pin, or other feature, to limit the depth of its entrance into a cannula. In addition, a delivery tube 14 may be configured to be affixed to, or lock into, a cannula so that, once introduced into the cannula, it may maintain its position for a desired period. A luer lock mechanism, a pin and slot arrangement, where a pin on the surface of the delivery tube 14 fits into and engages with a slot on a cannula, or other mechanism or mechanisms may be used to fix the position of a delivery tube 14 with respect to a cannula.

As illustrated in FIGS. 1A-1D, the present invention provides materials suitable for marking intracorporeal locations, and methods and apparatus for delivering such materials to desired intracorporeal locations. For example, particulate material 16 may be any ultrasound-detectable powder or other ultrasound-detectable aggregation of small particles. In some embodiments of the invention, particulate material 16 may include radiopaque elements or materials, MRI-detectable materials, pigments, dyes, or other materials as well. System 10 and apparatus 12 may be any system and apparatus suitable for delivering an ultrasound-detectable particulate material 16 to a location within a body. Any method effective to deliver an ultrasound-detectable particulate material is suitable for the practice of the invention.

Examples of materials, apparatus, systems, and methods embodying features of the invention are presented below. However, before presenting some features and embodiments illustrating the present invention, it is helpful to introduce some terms which are used in describing aspects of the invention.

The term "detectable" as used herein means able to be detected by a person, either with or without the use of imaging instrumentation (such as ultrasound imaging instrumentation). For example, a mass or material that is detectable by ultrasound is able to produce a readily recognizable image on the display apparatus of ultrasound imaging instrumentation. A material is "not readily detectable" within a patient if, for example, an ultrasound examination directed to the location where the material had been placed does not produce a readily recognizable ultrasound image. As used herein, "readily" means without the use of extreme or extraordinary measures or without requiring extraordinary skill.

"Bio-resorbable" as used herein means resorbable in a biological environment, such as within the body of a patient. A bio-resorbable material is thus a material which may be absorbed, dissolved, broken down, degraded, assimilated, or otherwise removed from a biological environment, such as from within the body of a patient. A bio-resorbable polymer is a polymeric material (including copolymers, alloys and polymer mixtures composed of two or more polymers) which is bio-resorbable.

The "in-vivo lifetime" of a bio-resorbable material as used herein refers to the period of time after placement of the material within the body of an animal that the material remains readily detectable. Thus, the "in-vivo lifetime" of an ultrasound-detectable bio-resorbable material is that period of time during which the material remains readily detectable within a patient by ultrasound.

The term "blowing agent" as used herein means a material or combination of materials present during the processing or compounding of a polymer material that produces or breaks down into a gas at processing temperatures or pressures. For example, where particles of polymer or copolymer material also contains a blowing agent, and the particles are heated, extruded, or otherwise processed, the blowing agent decomposes, vaporizes, or reacts to form a gas inside the material, producing cavities within the material. A blowing agent may be a solid, a liquid (such as a liquid that vaporizes at or below the processing temperature), or a gas. A blowing agent may be added to a material or mixture during processing, such as by directing pressurized gas into a mixing chamber or a reaction chamber. Biocompatible blowing agents are preferred.

A "bubble cavity" is an enclosed, sealed cavity within a material filled with a gas or air. A bubble cavity may be produced by gas that is present in a material or mixture during processing. For example, a gas may be present during processing where the gas has been introduced into the processing location; or where it has been evolved or produced by the materials present during processing; or it may have been released by materials present during processing. In particular, inclusion of a blowing agent during or after processing of a material or mixture of materials may aid or cause the production of bubble cavities.

"Particle size" as used herein describes the external physical dimensions of particles making up a population of small particles of a material, and may be determined, for example, by passing a powder through a sieve with a known nominal minimum passage dimension. As used herein, a powder of a given particle size will typically include particles of a wide range of sizes. For example, in an aggregation of particles having a nominal particle size of between about 100 microns to about 150 microns, more than about 80% of the particles (by weight) fall within the nominal range and up to about 20% do not. Thus, most, but not all of the particles usually fall within a nominal range described by the particle size of a powder.

"Gelatin" as used herein means a viscous, semi-solid, or solid material, also termed a "gelatinous" material. Gelatin is typically biologically-derived, although synthetic gelatin is also available. For example, gelatin may consist largely of collagen obtained from processed animal connective tissue. Vegetable gelatin such as agar is often made from kelp, algae, or other plant material. Gelatin may include bovine collagen, porcine collagen, ovine collagen, equine collagen, agar, synthetic gelatin such as synthetic human-derived collagen, and combinations of these.

"Bulk density" as used herein is defined as the quotient of the weight of a material, such as a powder, divided by the volume of the material.

A biocompatible liquid or fluid is a liquid that may be introduced into a patient's body without harming the patient. Sterile saline and sterile water containing a sugar (such as dextrose, sucrose or other sugar) or other suitable osmotically-active compounds are typical biocompatible liquids. Other liquids, including fluids not containing water, such as biocompatible oils, may also be used. A biocompatible liquid may be mixed with other agents or materials and used to carry contrast agents, colorants, markers, inert agents, and pharmaceutical agents into a patient.

Pharmaceutical agents, as used herein, are agents used to treat a disease, injury, or medical condition, and include, but are not limited to, drugs, antibiotics, cancer chemotherapy agents, hormones, anesthetic agents, hemostatic agents, and other medicinal compounds. Hemostatic agents are agents which tend to reduce bleeding, enhance clotting, or to cause vasoconstriction in a patient. Brachytherapy agents are typically sources of radiation for implantation near to the site of a cancerous lesion.

In one aspect, the invention provides a bio-resorbable material suitable for temporarily marking a biopsy site within a patient. Materials embodying features of the invention are detectable within a patient after introduction into a biopsy site, remain detectable for a period of time, and then are not detectable after the period of time. Such materials include bio-resorbable materials which are dissolved and absorbed into body tissue at or near to the biopsy site. Typically, such materials include a powder made from a bio-resorbable polymer such as poly-lactic acid, poly-glycolic acid, poly-caprolactone, and copolymers, alloys, mixtures of these polymers, and combinations of these materials.

Bio-resorbable polymeric materials suitable for use in making ultrasound-detectable biopsy marker materials typically have a bulk density of between about 0.8 g/ml and about 1.5 g/ml. Preferably, the bio-resorbable polymeric material is a foam or other material containing cavities, with a bulk density after processing of less than about 1 g/ml, more preferably between about 0.8 g/ml and about 1 g/ml.

An ultrasound-detectable marker typically must be remain in place and detectable within a patient for at least 2 weeks to have practical clinical value. Thus, an ultrasound-detectable marker material embodying features of the invention is detectable at a biopsy site within a patient for a time period of at least 2 weeks, preferably at least about 6 weeks, and may remain detectable for a time period of up to about 20 weeks, more preferably for a time period of up to about 12 weeks. An ultrasound-detectable marker material embodying features of the invention is preferably not detectable about 6 months after placement at a biopsy site. More preferably, an ultrasound-detectable marker material embodying features of the invention is not detectable with ultrasound about 12 weeks after placement at a biopsy site. A preferable in-vivo lifetime for an ultrasound-detectable biopsy marker mass having features of the invention is between about 6 weeks and about 12 weeks.

Typically, the ultrasound-detectable biopsy marker materials of the present invention are deposited at locations within a patient's body to form a biopsy marker mass. Thus, for example, a quantity of powder formed from comminuted material having finely divided particles with bubble cavities within the particles may be delivered into a cavity at a biopsy site. In some embodiments, the ultrasound-detectable biopsy marker materials form a gel mass upon being introduced within the body of a patient. These a gel masses may be flexible gels or may be rigid, solid gels. In preferred embodiments, the marker materials remain within the biopsy cavity and do not migrate. The marker materials are resorbed by tissue and fluids near the biopsy site, so that, after a limited time, the marker materials are no longer USI-detectable at the biopsy site. The limited time during which the marker materials remain USI-detectable is the in-vivo lifetime.

In addition, ultrasound-detectable biopsy marker materials embodying features of the invention may also include radiopaque materials or radiopaque elements, so that the biopsy site may be detected both with ultrasound and with X-ray or other radiographic imaging techniques. Radiopaque materials and markers may include metal objects such as clips, bands, strips, coils, and other objects made from radiopaque metals and metal alloys, and may also include powders or particulate masses of radiopaque materials. Radiopaque markers may be of any suitable shape or size, and are typically formed in a recognizable shape not naturally found within a patient's body, such as a star, square, rectangular, geometric, gamma, letter, coil or loop shape. Suitable radiopaque materials include stainless steel, platinum, gold, iridium, tantalum, tungsten, silver, rhodium, nickel, bismuth, other radiopaque metals, alloys and oxides of these metals, barium salts, iodine salts, iodinated materials, and combinations of these. Radiopaque materials and markers may be permanent, or may be temporary and not detectable after a period of time subsequent to their placement at a biopsy site within a patient.

In addition, ultrasound-detectable biopsy marker materials embodying features of the invention may also include MRI-detectable materials or markers, so that the biopsy site may be detected both with ultrasound and with MRI or other imaging techniques. MRI contrast agents such as gadolinium and gadolinium compounds, for example, are suitable for use with ultrasound-detectable biopsy marker materials embodying features of the invention. Colorants, such as dyes (e.g., methylene blue and carbon black) and pigments (e.g., barium sulfate), may also be included in ultrasound-detectable biopsy marker materials embodying features of the invention.

Cavity-containing particles embodying features of the invention may be made from a wide variety of biocompatible bio-resorbable material. Thus, cavity-containing particles formed from any material that is not toxic, and which is resorbable, may be used to form ultrasound-detectable bio-resorbable marker materials and compositions having features of the invention. Some particularly suitable materials include bio-resorbable polymers including, but not limited to, polymers of lactic acid, glycolic acid, caprolactones, and other monomers; thus, for example, suitable bio-resorbable polymers may include poly(esters), poly(hydroxy acids), poly(lactones), poly(amides), poly(ester-amides), poly(amino acids), poly(anhydrides), poly(ortho-esters), poly(carbonates), poly(phosphazines), poly(thioesters), poly(urethanes), poly(ester urethanes), polysaccharides, polylactic acid, polyglycolic acid, polycaproic acid, polybutyric acid, polyvaleric acid, and copolymers, polymer alloys, polymer mixtures, and combinations thereof.

The in-vivo lifetime of a polymeric material is related to the molecular weight of the polymer. For example, copolymers of lactic and glycolic acids having an initial molecular weight of about 60,000 daltons (60 kD) before processing, are suitable for use in making an ultrasound-detectable marker material having an in-vivo lifetime of about 12 weeks. The starting molecular weight degrades, during an extrusion process that adds gas bubbles to form bubble cavities in the polymeric material, thereby enhancing its detectability by ultrasound. The molecular weight further degrades to about 45,000 dalton (45 kD) following gamma-ray sterilization. As is known to those of ordinary skill in the art, other materials, including other polymeric materials, may require a different starting molecular weight in order to obtain the same in-vivo lifetime. For example, polyglycolic acid typically degrades faster than other materials and as such requires a substantially higher initial molecular weight than polylactic acid or polycaprolactone to obtain a similar in-vivo lifetime.

Comminution of polymers and other starting materials (which preferably are porous materials) by grinding, milling, pulverizing, or otherwise reducing the materials in size, is effective to form a powder. Ultrasound-detectable materials having features of the invention are typically powders having particle sizes of about 20 microns to about 2000 microns. The particles typically contain within them bubble cavities with sizes of between about 10 microns to about 500 microns.

The preferred particle size depends in one aspect on the inner diameter of a tube used to deliver the powder to a biopsy site. Larger particle sizes are more easily accommodated in larger diameter delivery tubes, while smaller delivery tubes may be used to deliver powders having smaller particle sizes. Where the delivery tube has an inner diameter of no greater than about 0.075 inches (1.9 mm), powders having particle sizes of between about 20 microns and about 800 microns, and more preferably between about 300 microns and about 500 microns, are preferred.

The starting materials may have, or may be processed to produce, bubbles which produce internal bubble cavities.

Comminution of the starting material provides small particles with pocked, pitted, and ridged surfaces formed from the exposed surfaces of broken bubble cavities. Many of the particles have internal voids formed of bubble cavities. Gas-filled or air-filled bubble cavities are effective to reflect ultrasound energy, and greatly enhance the ability of particles containing gas-filled or air-filled bubble cavities to be imageable by USI. The sizes of such bubble cavities may be measured by lengths across the cavities, through geometric centers of the cavity. Bubble cavity size is typically between about 10 microns and about 500 microns, preferably between about 20 microns to about 200 microns.

Materials embodying features of the invention may also include binding agents which help powder particles to adhere together and so to make the powder a more cohesive mass. Typical binding agents include gelatin, polyethylene glycol, polyvinyl alcohol, glycerin, acrylic hydrogels such as hydroxy ethyl methylacrylate, other organic hydrogels, and other hydrophilic materials. Binding agents may be used singly or in combination with other binding agents. In some embodiments of the invention, gelatin is a preferred binding agent. Gelatin suitable for use in materials embodying features of the invention includes bovine collagen, porcine collagen, ovine collagen, equine collagen, synthetic collagen, agar, synthetic agar, and combinations of these. Synthetic materials may be preferred in order to avoid raising concerns over possible allergies to bovine or porcine collagen. In some embodiments, a marker material includes (by weight) about one part gelatin to about two to five parts bio-resorbable polymeric material. In a preferred embodiment, a marker material includes about one part gelatin to about three to four parts bio-resorbable polymeric material (by weight)

Many properties of a marker material affect the intensity of its ultrasound reflection, including density, physical structure, molecular material, and shape. For example, sharp edges, or multiple reflecting surfaces on or within an object differing in density from its surroundings enhances a marker's ability to be detected by ultrasound. Interfaces separating materials of different densities, such as between a solid and a gas, produce strong ultrasound signals. The methods of the present invention provide marker materials effective to produce strong ultrasound signals, the marker materials having gas-containing bubble cavities.

Marker materials with a high degree of porosity, whether from bubbles formed in situ during manufacture of the material, or from bubbles trapped within the material during later processing, provide strong ultrasound signals when located within the body of an animal which translates to improved ultrasound imaging. Starting material having gas bubbles entrained within it may be ground and sieved to obtain powders providing strong ultrasound signals. Portions of the powders may be selected to have particle sizes within a desired size range.

Figure 2A:
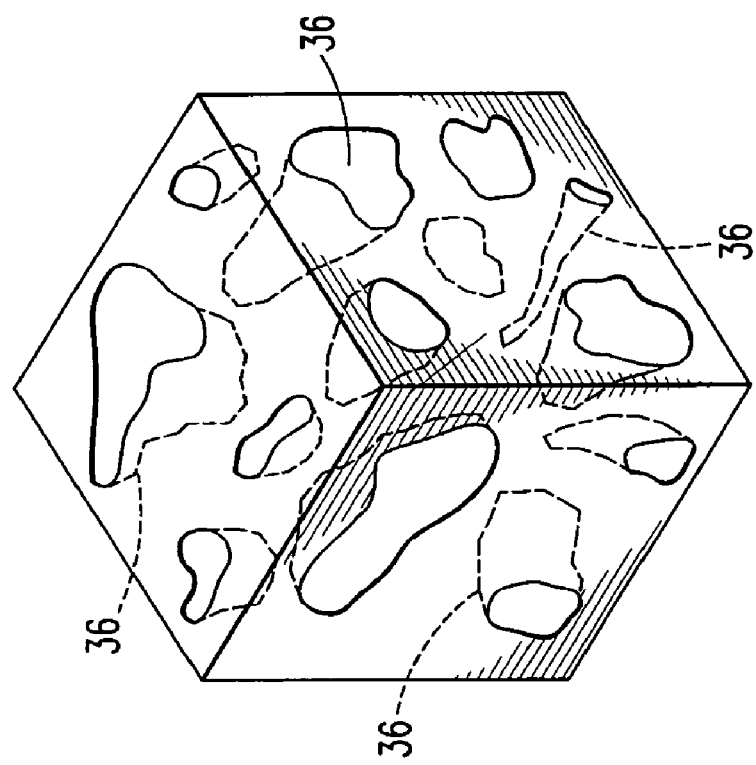
FIG. 2A is a perspective view illustrating a cubic section of a material having bubble cavities (indicated with dotted lines).

A cubic section of a material having internal bubble cavities is illustrated in perspective view in FIG. 2A. Internal bubble cavities 36 are indicated by dotted lines. Comminution (i.e., grinding, pulverizing, or otherwise reducing to small particles) of such a material into particles containing bubble cavities produces an ultrasound-detectable material suitable for marking an intracorporeal location. The particles resulting from such comminution form an aggregation (which may be termed a powder) which may be deposited within a body. An illustration of one such particle is shown in FIG. 2B, which is at a smaller scale than FIG. 2A.

Gas bubbles can be introduced into a material by whipping a gas into the material during processing of a material, by release of gas from within the material, or by directing a gas into a material. Alternatively, bubbles within a material may be created by secondary processing such as extruding a polymer and a blowing agent together to create a rod having gas bubbles entrained within it. A blowing agent may decompose to release a gas, or may react with other materials to form a gas. For example, a blowing agent that breaks down into a gas at elevated processing temperatures or pressures may be included in a mixture in order to produce bubbles within a material. The material produced after introduction of such bubbles is one riddled with bubble cavities, forming a foam or sponge-like structure.

Blowing agents suitable for practicing the methods of the invention include, but are not limited to, sodium bicarbonate, ammonium carbonate, and other carbonates; sodium boron hydride, silicon oxy-hydride, and other hydrides; hydrochlorofluorocarbon compounds, and chlorofluorocarbon compounds. Liquid blowing agents, such as hydrocarbons and alcohols, may also be used. For example, for polymers having molecular weights of up to about 60 kD, liquid blowing agents, particularly hydrocarbons and alcohols having boiling points in the range of between about 75° C. and about 95° C., are suitable for the practice of the invention. Such blowing agents include, but are not limited to, hexane, heptane, heptene, propyl alcohol, isopropyl alcohol, other hydrocarbons and alcohols, and mixtures of hydrocarbons and alcohols. Biocompatible blowing agents are preferred blowing agents.

Sodium bicarbonate is a presently preferred blowing agent; it has a broad and relatively low decomposition temperature well within the processing parameters of typical bio-resorbable polymeric materials. Mixtures of sodium bicarbonate and polymeric material usually include less than about 10% by weight sodium bicarbonate, and typically include no greater than about 5% sodium bicarbonate by weight. In a preferred embodiment of the methods of the present invention, about 2% by weight sodium bicarbonate is combined with polylactic acid and polyglycolic acid copolymer, and the combination is extruded to form a rod.

Mixtures of polymers such as polylactic acid, polyglycolic acid, polycaprolactone, their co-polymers, and the like, with about 2% by weight of a blowing agent such as sodium bicarbonate, produce gas bubbles that vary in size between about 10 microns and about 500 microns, preferably about 20 microns to about 200 microns, with most bubbles averaging about 100 microns in size. The bubbles are typically not spherical in shape, but are generally elongated and distorted, due to the shear applied to the material as it moves though the extrusion die and due to the tension applied to the material in its plastic state. The exterior of rods extruded during processing is typically found to be bumpy. This surface texture is produced as a result of the bubbles being distorted from this process as well as surface bubbles swelling and bursting as the pressure is relieved from within the extrusion melt chamber.

The bulk density of raw polymeric material suitable for the practice of the invention is typically about 1.3 g/ml before processing. A preferred raw polymeric material is a mixture of polylactic acid (PLA) and polyglycolic acid (PGA) in a ratio of 65% to 35% (PLA:PGA) by weight. The bulk density of the processed material can be varied from about 0.8 g/ml to about 1.5 g/ml to obtain a material which has the desired ultrasound characteristics. This variation can be obtained by increasing the proportion of blowing agent in the mix (for example, up to about 5% sodium bicarbonate by weight), by processing the extrusion at a higher temperature, or both. A lower bulk density material may be produced by either variation of the method (i.e., by increasing blowing agent or increasing extrusion temperature). The effect of lowering the density of the processed material is to increase the fragility of the extruded rod, to reduce the amount of material required, and to reduce its in-vivo lifetime.

Inclusion of excessive amounts of blowing agent (e.g., typically greater than about 10% by weight in PLA:PGA mixtures) tended to produce processed material that was mostly gas surrounded by very thin layers of polymer. Such material was not as suitable for use in an ultrasound-detectable biopsy site marker material as more dense materials. These materials produced with excessive amounts of blowing agent had relatively thin polymer structures that degraded more rapidly than thicker structures, and also tended to lose gas from the bubble cavities, which then tended to collapse so that the desirable ultrasound characteristics of the material was lost. Lower amounts of blowing agent (e.g., less than about 10%, preferably not greater than about 5%, more preferably about 2%, blowing agent by weight included with polymers and copolymers of polylactic acid, polyglycolic acid, and polycaprolactone) so as to provide material having a bulk density of about 0.8 g/ml to about 1.5 g/ml, preferably about 1.0 g/ml or less, provided materials having the desired ultrasound signal properties and the desired in-vivo lifetime.

A binding agent can be added to the marker material to make the powder a more cohesive mass. Materials such as porcine gelatin, bovine gelatin, polyethylene glycol, polyvinyl alcohol, glycerin, or other hydrophilic material are suitable for use in materials having features of the invention. One desirable characteristic of binding agent materials is to keep the powder from dispersing away from the biopsy site following delivery at the biopsy site. In general, the amount of binding agent is much less than the amount of ultrasound-detectable bio-resorbable powder. For example, a suitable mixture is one part porcine gelatin to 3 parts bio-resorbable ultrasound visible powder.

A typical human breast has a substantial number of features that are visualized with ultrasound. These features all have characteristic signals. Fibrous tissue or ligaments tend to show up as bright streaks, fat seems to appear as a dark gray area, the glandular tissue appears as a mottled medium gray mass. Cancerous lesions typically appear as a darker area with a rough outer edge which has reduced through transmission of the ultrasound energy.

However, due to the large amount of fibrous tissue normally present in a human breast, and due to the presence of ligaments running through the breast, a marker that simply has a bright signal alone will not provide a useful signal that can is readily discernable from the many anatomic features normally present within a human breast. Such markers are typically small, being sized to fit within a syringe or other delivery tube, and so are often not readily distinguishable from natural features of the breast, which include occasional small ultrasound-bright spots. One advantage of the ultrasound-detectable biopsy marker materials of the present invention is that the materials provide an ultrasound signal which can be readily differentiated from anatomic structures within the breast, so that the identification and marking of a biopsy cavity does not require extensive training and experience.

The gas bubbles within the materials processed as described herein form bubble cavities within the material that create a bright (white) mark or signal when viewed with ultrasound, enhancing the strength of the ultrasound signal intrinsic to the polymeric material itself. The rough edges of fractured or partial cavities may also help to enhance the ultrasound image. In addition to providing a strong ultrasound signal, the gas bubbles also effectively stop transmission of the ultrasound signal, creating a shadow behind the bright spot.

FIG. 2B is a perspective view of a particle of an ultrasound-detectable bio-resorbable marker material embodying features of the invention, having an enclosed bubble cavity 36 indicated with dotted lines. The surface of the particle illustrated in the figure is irregular, having curved indentations, rounded features, and jagged edges. Particles of ultrasound-detectable finely-divided particulate materials having features of the invention have a variety of shapes and surface features, not all particles having the same shapes and features. Many, preferably a majority, of the particles of ultrasound-detectable finely-divided particulate materials having features of the invention include at least one bubble cavity. The bubble cavity may be of any size or shape. The size of a bubble cavity may be determined by measuring a distance along a line passing between one surface of the cavity, through a geometric center of the cavity, to another surface of the cavity. Preferably, most bubble cavities have a size between about 10 microns and about 500 microns, more preferably between about 50 microns and about 200 microns.

The biopsy marker materials of the present invention include ultrasound-detectable bio-resorbable particulate material and may also include a biocompatible fluid vehicle which helps to carry the powder to the biopsy site. When deposited at a cavity at an intracorporeal location, the ultrasound-detectable marker material, with or without a carrier fluid, is able to fill the entire cavity. For example, where the cavity is a biopsy cavity left after removal of a biopsy sample from a breast, the size of the ultrasound-detectable marker can be as large as the biopsy sample that was removed from the breast, which makes it much easier to distinguish the ultrasound signal of the marker from signals arising naturally from within a breast.

Thus, the ultrasound-detectable biopsy site marker materials of the present invention provide several advantages over prior markers. For example, the gas bubbles and bubble cavities within the material show up as a bright spot which allow for it to be distinguished from background anatomy. At the same time, the gas bubbles and bubble cavities produce a shadow below the bright spot. Thirdly, filling a biopsy cavity with the ultrasound marker outlines the entire biopsy site. When used with a Mammotome® or SenoCor 360™ biopsy, the marker mass creates a large curved bright upper surface which matches the outline of the biopsy cavity, and a shadow below this surface.

Ultrasound-detectable biopsy marker materials having features of the present invention may be made by any suitable method, including the methods described below. For example, ultrasound-detectable biopsy marker materials having features of the present invention may be made by reducing a bio-resorbable material having bubble cavities to a powder. A material may be reduced to a powder by granulating it, as by grinding the material, chopping the material, subjecting the material to the impact of a hard tool, impacting the material onto a hard surface, agitating the material, or by other methods known in the art. The starting material may include colorants, contrast agents, and other materials if desired.

Cryogrinding is a suitable method of comminuting a material to produce bio-resorbable ultrasound-detectable marker materials having features of the invention. A starting block of material may be frozen, for example by exposure to a liquified gas such as liquid nitrogen, and then pounded or beaten to shatter the block into smaller pieces, which may then be ground between grinding plates to reduce the pieces to a desired particle size.

Comminution of the material is continued until a powder having a particle size of less than about 2000 microns is produced. Preferably, the comminution is effective to provide a powdered biopsy marker material having a particle size of between about 20 microns and about 800 microns, more preferably between about 300 microns and about 500 microns. Typically, the resulting powder flows freely when poured. It may be stored as a dry powder. Powdered pigment, contrast agent, or other particulate material may also be included at this stage if desired.

Granulation and powdering typically produce a wide range of particle sizes. A method of selecting particles of a desired size is to pass the powdered material through a sieve. For example, a powder resulting from granulation may be loaded onto a sieve having a desired sieve size, and particles collected from beneath the sieve after passing through the sieve. This will separate the powder into two portions: a first portion retained by, the sieve, and thus apparently unable to pass through it, and a second portion that has passed through the sieve. The second portion that has passed through the sieve consists of particles having particle sizes less than the sieve size of the sieve. Thus, for example, a powder having a particle size of less than about 2000 microns may be collected by passing a powder through a sieve having a sieve size of 2000 microns, and a powder having a particle size of less than about 800 microns may be collected by passing a powder through a sieve having a sieve size of 800 microns.

Multiple sieves may be used in a conventional fashion to separate the powder into different size particle portions. For example, passing a powder through a first sieve with a larger sieve size, and then passing the resulting powder through a second sieve having a smaller sieve size can separate out a powder portion having particle sizes falling between the first sieve size and the second sieve size.

In preferred embodiments, the bio-resorbable material is a bio-resorbable polymeric material. Suitable polymeric materials include polylactic acid, polyglycolic acid, polycaprolactone, and combinations of these polymers. Polymeric mixtures may include copolymers and alloys of bio-resorbable polymers. The bio-resorbable material or materials used to make ultrasound-detectable biopsy site marker materials having features of the present invention preferably have bubble cavities. One way to characterize bubble cavities is to describe the cavity size, which is defined by an average length of a population of, cavities in a material. Where only a portion of what once was a larger bubble cavity remains, cavity size is measured by a length spanning the existing portion of the cavity. Cavity size may be measured, for example, by examination of the material with an optical microscope, preferably using an eyepiece with a reticle, or by inspection of electron micrographs of specimens of a material. Materials suitable for the practice of the invention have a cavity size of about 2000 microns or less. Preferred materials have a cavity size of between about 10 microns and about 500 microns, more preferably the cavity size is between about 20 microns and about 200 microns.

Bubble cavities may be introduced into a material during processing by any suitable method. For example, bubble cavities may be introduced into a polymeric material by whipping a gas into a polymeric material while the material is heated and in a plastic or malleable state. Gas may be introduced by providing a source of high pressure gas, such as nitrogen or argon, and directing the gas into a mixing chamber containing heated polymeric material.

Another suitable method for providing a material having bubble cavities is to mix a material and a blowing agent, preferably a biocompatible blowing agent, and to extrude the material and a blowing agent together. For example, extrusion of a polymeric material and a blowing agent will create a polymeric rod having gas bubbles entrained within it. These bubbles will typically not have a spherical shape, but instead may be elongated or irregular, due to the shear forces experienced during extrusion. Thus, for example, an ultrasound-detectable biopsy marker material may be made by extruding a polymeric material and a blowing agent to provide a bio-resorbable polymeric material having bubble cavities, and then reducing the material to a powder. Typically, a mixture of polymer and blowing agent should include less than about 10% by weight of the blowing agent, preferably no more than about 5%, most preferably about 2%. Suitable blowing agents include sodium bicarbonate, ammonium carbonate, sodium boron hydride, silicon oxy-hydride, hydrochlorofluorocarbon compounds, chlorofluorocarbon compounds, mixtures of sodium bicarbonate, ammonium carbonate, sodium boron hydride, silicon oxy-hydride, hydrochlorofluorocarbon compounds, and chlorofluorocarbon compounds, hexane, heptane, heptene, propyl alcohol, isopropyl alcohol, other hydrocarbons and alcohols, and mixtures of hydrocarbons and alcohols.

Sodium bicarbonate is a preferred blowing agent. In one embodiment of the methods of the invention, an ultrasound-detectable biopsy marker material may be made by extruding a copolymer of poly-lactic acid and poly-glycolic acid with sodium bicarbonate. The amount of sodium bicarbonate should make up less than about 10%, and preferably not more than about 5%, of the total starting material weight. More preferably sodium bicarbonate makes up about 2% of the total starting material weight of the mixture.

Alternative methods of making a material having cavities are also suitable. For example, a powder of material dissolvable in water or other solvent may be mixed into a polymer matrix to create a polymer encapsulating the dissolvable powder, and the polymer matrix containing the powder then exposed to the solvent. The solvent dissolves the powder out of the polymer matrix, leaving cavities, thus creating a porous polymer. Suitable powder materials for use in practicing this method include salts such as sodium chloride, potassium chloride, calcium chloride and other salts, sugars such as glucose, sucrose, and other water-soluble sugars, and the like. Comminution of the polymer matrix may be performed either before or after dissolving out the powder; preferably, comminution of the polymer matrix is performed after dissolution of the encapsulated powder.

Similarly, a slurry can be made of a dispersion of a polymer (which could also be a copolymer, polymer alloy, polymer mixture, or combination of these) and a dissolvable powder (such as a salt or a sugar, as described above). The slurry can be cast to provide a solid material of polymer with dissolvable powder inclusions, and the powder then dissolved by exposing the cast material to a solvent. The inclusions need not be solid; an emulsion made up of a polymer (which could also be a copolymer, polymer alloy, polymer mixture, or combination of these) and a non-miscible liquid can be cast to provide a solid with included droplets of the non-miscible liquid. The non-miscible liquid may then be extracted so that the solid material becomes a foam. For example, a non-miscible liquid may be extracted by exposing the cast material to low pressure, or by freeze-drying the cast material in a low-temperature, low pressure environment, allowing the non-miscible liquid to escape from the cast material by diffusion.

In addition, an ultrasound-detectable biopsy marker material having features of the present invention may include a binding agent with the powder. A binding agent helps to keep the powder together during deposition at a biopsy site. Suitable binding agents include gelatin, polyethylene glycol, polyvinyl alcohol, glycerin, other hydrophilic materials, and combinations of these. Suitable gelatins include bovine collagen, porcine collagen, ovine collagen, equine collagen, synthetic collagen, agar, synthetic gelatin, and combinations of these.

Biopsy site marker materials having features of the present invention may be delivered to a biopsy site in dry form, or in wet form, as in a slurry or suspension. Pressure may be applied to the powder in order to eject it from a storage location, such as a delivery tube. Pressure effective to deliver an ultrasound-detectable bio-resorbable marker material having features of the invention includes gas pressure, acoustic pressure, hydraulic pressure, and mechanical pressure. For example, dry ultrasound-detectable bio-resorbable powders may be blown into a biopsy site by the action of gas pressure from a pressurized gas directed behind or alongside the powder and towards the biopsy site. Such gas pressure may be supplied by carbon dioxide or nitrogen gas contained within a pressure vessel under high pressure, and the pressure released into a chamber containing a dry ultrasound-detectable bio-resorbable powder effective to drive the powder through an attached needle or catheter having an orifice within a biopsy site. Alternatively, a syringe filled with air or other gas may be connected to a tube or chamber containing an ultrasound-detectable bio-resorbable powder and the syringe plunger depressed so as to force the air or gas, and the powder, through a needle or catheter attached to the tube or chamber and having an orifice within a biopsy site. It will be understood that any device for providing gas or liquid flow through a delivery tube containing an ultrasound-detectable bio-resorbable powder is suitable to deliver a bio-resorbable marker mass to a desired location within a patient's body.

Mechanical pressure may be delivered by, for example, direct contact with a plunger. Where the particle size is significant relative to the diameter of a delivery tube, an ultrasound-detectable bio-resorbable powder having features of the invention may be expelled from the tube by directly pushing on it with a plunger. Thus, for example, where the particle size of such a powder is within a range of between about 60% to about 90% of the inner diameter of the delivery tube bore, a quantity of powder within the delivery tube may be expelled by direct action of a plunger on the powder without need for liquid or gas. Alternatively, acoustic pressure supplied by, for example, an ultrasound transducer, may be used to deliver an ultrasound-detectable bio-resorbable powder having features of the invention.

A preferred method for delivering an ultrasound-detectable bio-resorbable powder to a biopsy site utilizes a biocompatible liquid to drive or carry the powder into the biopsy cavity at the biopsy site. For example, a quantity of ultrasound-detectable bio-resorbable powder may be contained within a tube or chamber that leads directly or indirectly to a biopsy site. The powder may be dispensed by the application of hydraulic pressure applied by a syringe containing sterile saline or other suitable liquid. Flow of the liquid carries the powder into the biopsy site; turbulence acts to mix the dry powder with the liquid to provide a slurry or suspension and to provide a fairly uniform distribution of the powder throughout the biopsy cavity. The syringe is preferably configured to tightly engage with the tube or chamber, in order to prevent leakage and to insure sufficient pressure and flow is directed towards the biopsy site. The tube or chamber containing the ultrasound-detectable bio-resorbable powder may be an elongated hollow tube, having a bore completely filled with the powder; or an elongated hollow tube, having a bore partially filled with the powder; or a chamber having internal dimensions that change along the length, configured to hold a desired quantity of ultrasound-detectable bio-resorbable powder and to provide a desired amount of mixing with the fluid.

In a most preferred embodiment, the quantity of ultrasound-detectable bio-resorbable powder is contained within a tube termed a "delivery tube." The tube has an outside diameter that is sized to fit within a cannula, such as a Mammotome® or SenoCor 360™ cannula. For example, a suitable delivery tube has an outside diameter (OD) of about 0.096 inches and has an inner diameter (ID) of about 0.074 inches. Other sizes are also suitable, the exact dimensions depending on the biopsy device used. In addition, a delivery tube may have markings to aid in determining the depth of the tube within a cannula, surface features (such as pins, slots, bumps, bars, wedges, luer-lock fittings, or bands, including a substantially conical circumferential band) effective to control the depth into which a delivery tube is fitted within a cannula or effective to lock a delivery tube into position within a cannula. For example, a delivery tube may have pins or bumps configured to engage a slot or a leading edge of a cannula, or a luer-lock fitting configured to lock into a cannula.

A cannula may also be configured to receive and to engage a delivery tube. A cannula may have pins, slots, wedges, bumps, bands, luer-lock fittings, or the like, to engage a delivery tube and to hold it into a desired position within the cannula. For example, a cannula may have a luer-lock fitting, or a slot to engage a pin on a delivery tube, or an internal bump wedge or band that limits the distance of travel of the delivery tube within the cannula.

Delivery tubes embodying features of the present invention may be made of any suitable bio-compatible material. Preferably, the material has sufficient strength to withstand the hydraulic pressure required to dispense the material (typically greater than 100 psi) and is able to be sterilized. A polyether block amide such as a Pebax®, preferably a 72 Durometer Pebax®, is one example of a suitable material. Hydraulic pressure may be supplied by depressing the plunger of a syringe, such as a 1 to 3 cc syringe, containing a suitable fluid and connected to the delivery tube. The amount of material required within the delivery tube will vary depending on the biopsy cavity size. Typically, quantities of between about 0.2 to about 1.2 ml of powder will be required. In many cases, a quantity of about 0.5 ml of the powder is suitable.

The delivery tube can be sized to accept any volume desired to be injected into the biopsy cavity. The average Mammotome® biopsy removes about 1 ml of tissue. The present inventors have found that about 0.5 ml of dry powder works best to fill such a biopsy cavity with the powder and fluid. Use of more powder typically leads to some filling of the needle track as well as of the cavity at the biopsy site. Smaller volumes of powder may be used for smaller cavities at a biopsy site, such as are created with an automated Tru-Cut® biopsy or a single SenoCor 360™ biopsy, available from SenoRx, the assignee of the present invention.

Ultrasound-detectable bio-resorbable powder may be loaded into an delivery tube in preparation for use in marking a biopsy site. The delivery tube may be attached to a syringe having about 0.5 ml to about 2 ml of fluid, preferably about 1.0 ml to about 1.5 ml of fluid, at any suitable time before delivery to a biopsy site. After a biopsy has been taken from a biopsy site within a patient, the delivery tube is placed with its distal end at or directed to the biopsy site, typically by placing the delivery tube within a cannula leading to the biopsy site, and the powder is then dispensed by directing the fluid through the delivery tube, so that it is thereby deposited at the biopsy site.

Alternatively, a syringe could be loaded with an ultrasound-detectable bio-resorbable powder having features of the invention, filled with a biocompatible fluid, and then shaken or stirred to create a slurry. The syringe may then be connected to a delivery tube or catheter, and the slurry injected through the delivery tube or catheter to fill the biopsy site with an ultrasound-detectable bio-resorbable marker composition.

When mixed with a suitable fluid, ultrasound-detectable bio-resorbable powders having features of the invention may form a suspension, which may be dilute or concentrated, depending on the relative amounts of fluid and of powder. A concentrated suspension may be termed a slurry, and may be somewhat viscous and have the consistency of a paste. The consistency of the suspensions may change with time; for example, a suspension of an ultrasound-detectable bio-resorbable powder having features of the invention may set up over time to form a semi-solid gel. Inclusion of a binding agent such as gelatin, preferably an amount of gelatin of about 5% to about 50% by weight, is effective to help gel formation after mixing an ultrasound-detectable bio-resorbable powder with a suitable fluid. Gelatin typically hardens to its ultimate firmness within minutes at normal body temperature.

The fluid used to deposit the powder at a biopsy site may contain other agents, including inert agents, osmotically active agents, pharmaceutical agents, and other bio-active agents. For example, a suitable biocompatible liquid may be selected from the group consisting of sterile saline, sterile saline containing a pharmaceutical agent, sterile saline containing an anesthetic agent, sterile saline containing a hemostatic agent, sterile saline containing a colorant, sterile saline containing a radio contrast agent, sterile sugar solution, sterile sugar solution containing a pharmaceutical agent, sterile sugar solution containing an anesthetic agent, sterile sugar solution containing a hemostatic agent, sterile sugar solution containing a colorant, sterile sugar solution containing a radio contrast agent, biocompatible oils, biocompatible oils containing a pharmaceutical agent, biocompatible oils containing an anesthetic agent, biocompatible oils containing a hemostatic agent, biocompatible oils containing a radio contrast agent, and biocompatible oils containing a colorant. For example, anesthetic agents may be beneficial by reducing patient discomfort.

Hemostatic agents tend to reduce bleeding, enhance clotting, or to cause vasoconstriction in a patient. Hemostatic agents include adrenochrome, algin, alginic acid, aminocaproic acid, batroxobin, carbazochrome salicylate, cephalins, cotarmine, ellagic acid, epinephrine, ethamsylate, factor VIII, factor IX, factor XIII, fibrin, fibrinogen, naphthoquinone, oxamarin, oxidized cellulose, styptic collodion, sulamrin, thrombin, thromboplastin (factor III), tolonium chloride, tranexamic acid, and vasopression.

Pharmaceutical agents are often used to promote healing, and to treat injury, infection, and diseases such as cancer, and may include hormones, hemostatic agents and anesthetics as well as antibacterial, antiviral, antifungal, anticancer, and other medicinal agents. Pharmaceutical agents may be included as part of an ultrasound-detectable bioresorbable material placed within a biopsy cavity in order, for example, to promote healing, prevent infection, and to help treat any cancer cells remaining near the biopsy site.

Thus, pharmaceutical agents which may be included with a fluid or with a powder to form an ultrasound-detectable bioresorbable material having features of the invention include, but are not limited to: penicillins, cephalosporins, vancomycins, aminoglycosides, quinolones, polymyxins, erythromycins, tetracyclines, streptomycins, sulfa drugs, chloramphenicols, clindamycins, lincomycins, sulfonamides, paclitaxel, docetaxel, acetyl sulfisoxazole, alkylating agents, antimetabolites, plant alkaloids, mechlorethamine, chlorambucil, cyclophosphamide, melphalan, ifosfamide, methotrexate, 6-mercaptopurine, 5-fluorouracil, cytarabine, vinblastine, vincristine, etoposide, doxorubicin, daunomycin, bleomycin, mitomycin, carmustine, lomustine, cisplatin, interferon, asparaginase, tamoxifen, flutamide, amantadines, rimantadines, ribavirins, idoxuridines, vidarabines, trifluridines, acyclovirs, ganciclovirs, zidovudines, foscarnets, interferons, prochlorperzine edisylate, ferrous sulfate, aminocaproic acid, mecamylamine hydrochloride, procainamide hydrochloride, isoproterenol sulfate, phenmetrazine hydrochloride, bethanechol chloride, methacholine chloride, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, isofluorophate, acetazolamide, methazolamide, bendroflumethiazide, chloropromaide, tolazamide, chlormadinone acetate, phenaglycodol, allopurinol, aluminum aspirin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17-hydroxyprogesterone acetate compounds, 19-nor-progesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, dihydroxyphenylalanine, theophylline, calcium gluconate, ketoprofen, ibuprofen, cephalexin, haloperidol, zomepirac, ferrous lactate, vincamine, diazepam, phenoxybenzamine, milrinone, capropril, mandol, quanbenz, hydrochlorothiazide, ranitidine, flurbiprofen, fenufen, fluprofen, tolmetin, alclofenac, mefenamic, flufenamic, difuinal, nizatidine, sucralfate, etintidine, tetratolol, minoxidil, chlordiazepoxide, diazepam, amitriptyline, imipramine, prostaglandins, coagulation factors, analogs and derivatives of these compounds, and pharmaceutically acceptable salts of these compounds, or their analogs or derivatives.

Some possible components and combinations of components suitable for use in ultrasound-detectable bio-resorbable marker materials having features of the invention are presented in the following table. Comments are presented regarding the effects of including either a low percentage or a high percentage of the indicated components in a material made up of a mixture of components.

TABLE

| Component | Function | Low Percentage in the Mixture | High Percentage in the Mixture |
| --- | --- | --- | --- |
| Bio-resorbable polymer | Ultrasound marker with predetermined in- | Lightens the ultrasonic contrast, | Increases the ultrasound contrast to |

TABLE-continued

| Component | Function | Low Percentage in the Mixture | High Percentage in the Mixture |
|---|---|---|---|
| | vivo lifetime | creating a more USI translucent image of the filled cavity | create a USI-opaque image of the filled cavity |
| Binding agent | Reduces settling or particulate segregation | Forms a thinner slurry which makes delivery into the biopsy cavity easier; may also help control the relative density of the ultrasound marker | Forms a thicker slurry which doesn't easily displace from the biopsy cavity |
| Radiographic marker material or objects | Permanent radiographic biopsy-site marker | Not present - no radiographic marking | Provides permanent radiographic marking |
| Biocompatible fluid | Aids in delivering particulate mass and in forming a slurry | Thicker slurry, which doesn't easily displace from cavity | Thinner slurry, makes deposition into cavity easier; may also help control the relative density of ultrasound contrast agent |
| Hemostatic agent | Stops bleeding inside cavity | Stops light bleeding | Stops heavy bleeding |
| Anesthetic | Controls pain during and after procedure | Controls pain during procedure | Controls pain during and after procedure |
| Radiographic contrast agent | Defines size, shape, boundaries of biopsy cavity for radiographic imaging | Provide light amount of radiopacity within cavity; transient in nature | Provide dense radiopacity within cavity; transient in nature |
| Colorant | Visual cavity marking | Little or no visual marking of cavity | Dark visual marking of cavity |

An assembly for delivering an ultrasound-detectable bio-resorbable powder includes an delivery tube configured to be received within a biopsy guide cannula. Such a delivery tube is also configured to engage a syringe, and to hold a quantity of ultrasound-detectable bio-resorbable powder. The delivery tube may be configured to hold a quantity of ultrasound-detectable bio-resorbable powder by having an inner volume of between about 0.2 ml and about 1.2 ml, preferably between about 0.5 ml and about 1.0 ml. A delivery tube having features of the invention may also be configured to fit within a biopsy guide cannula, such as a Mammotome® guide cannula, a SenoCor 360™ cannula, or a Tru-Cut® cannula. For example, a delivery tube having an outside diameter less than about 0.1 inch (2.54 mm) is able to fit within a Mammotome® guide cannula. In addition, a delivery tube having features of the invention may also be configured to sealingly engage with a syringe, that is, to form a strong, water-tight connection. An example of a suitable connection is a luer-lock connection configured to sealingly engage with a syringe.

In further embodiments of the invention, a system for temporarily marking a biopsy site within a patient is provided. Such a system includes a syringe; a supply of ultrasound-detectable bio-resorbable powder; and a delivery tube configured to engage the syringe. Preferably, the engagement between the syringe and delivery tube is water-tight engagement, and is sufficiently strong as to withstand the hydraulic pressure generated by depressing the syringe plunger and directing fluid within the syringe through the delivery tube effective to deposit ultrasound-detectable bio-resorbable powder at the biopsy site. The supply of ultrasound-detectable bio-resorbable powder may be in a packet, a syringe, a delivery tube, or other container. In preferred embodiments of the system, the supply of ultrasound-detectable bio-resorbable powder is located within the delivery tube. The delivery tube is preferably configured to be received within a biopsy guide cannula. In more preferred embodiments, the delivery tube has an outside diameter of less than about 0.1 inch (2.54 mm). The system may further include a supply of biocompatible liquid, which is preferably sterile saline. More preferably, the biocompatible liquid is contained within the syringe of the system for ease of use and to avoid the possibility of spillage or contamination.

Figures 3A, 3B:
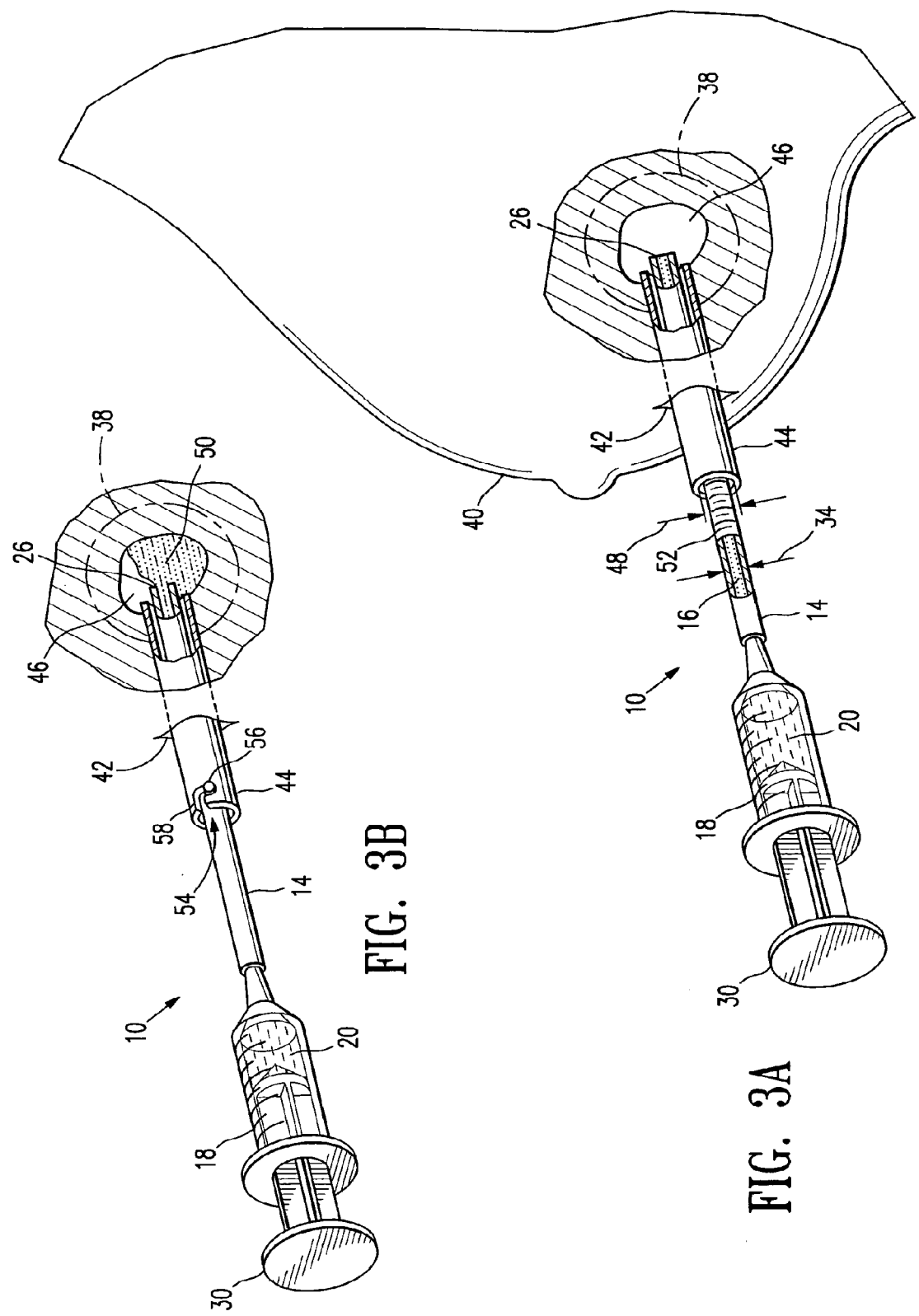
FIG. 3A is a partially cut-away, perspective view of a system as illustrated in FIG. 1 shown ready to deposit an ultrasound-detectable bio-resorbable marker material embodying features of the invention at a biopsy site within a breast of a patient.
FIG. 3B is a partially cut-away, perspective view of a system as illustrated in FIG. 3A shown in use as it deposits an ultrasound-detectable bio-resorbable marker material embodying features of the invention at a biopsy site within a breast of a patient.

FIG. 3A is a partially cut-away perspective view of a system 10 as illustrated in FIG. 1, shown ready to deposit an ultrasound-detectable bio-resorbable powder 16 within a cavity 46 at a biopsy site 38. FIG. 3B shows the system, following depression of plunger 30, as it deposits an ultrasound-detectable bio-resorbable marker material 50 embodying features of the invention (which includes ultrasound-detectable bio-resorbable powder 16 mixed with fluid 20) at a biopsy site 38 within a breast 40 of a patient.

An incision 42 in the breast allows access to biopsy site 38. Biopsy guide cannula 44 extends through incision 42 into cavity 46 at biopsy site 38. Syringe 18, containing a biocompatible fluid 20, is tightly engaged with a delivery tube 14, which extends within guide cannula 44 so as to locate delivery tube outlet 26 within biopsy site cavity 46. Delivery tube outer diameter 34 is configured to allow delivery tube 14 to fit inside the inner diameter 48 of biopsy guide cannula 44. Markings 52 (shown in FIG. 3A) spaced at regular intervals along the outer surface of delivery tube 14 indicate the depth of insertion of the tube within the cannula and aid in the proper placement of delivery tube outlet 26 into position within cavity 46. Depression of plunger 30 forces fluid 20 out of syringe 18 through delivery tube 14, where fluid 20 mixes with and carries ultrasound-detectable bio-resorbable powder 16 out of delivery tube outlet 26 to deposit ultrasound-detectable bio-resorbable biopsy site marker material 50 within cavity 46 at biopsy site 38. As shown in FIG. 3B, an optional locking mechanism 54, including pin 56 (on delivery tube 14) configured to engage with slot 58 (on cannula 44) may be used to fix delivery tube 14 in position within cannula 44 and to help prevent movement of delivery tube outlet 26 relative to cannula 44 when plunger 30 is depressed.

What is claimed is:

1. An ultrasound-detectable biopsy marker mass which has a detectable in-vivo lifetime during which the marker mass remains readily detectable by ultrasound, and which is formed of particles of a bio-resorbable material having bubble cavities inside the particles and having a particle size between about 200 microns and about 500 microns.

2. The ultrasound-detectable biopsy marker mass of claim 1, wherein the marker mass is a bio-resorbable powder mass having a volume of between about 0.2 ml and about 1.2 ml of powder.

3. The ultrasound-detectable biopsy marker mass of claim 1, the bubble cavities having a size of at least 50 microns, wherein the bubble cavities have geometric centers and the cavity size is measured by length through the geometric centers of the cavities.

4. The ultrasound-detectable biopsy marker mass of claim 1, wherein said bio-resorbable material comprises a bio-resorbable polymeric material.

5. The ultrasound-detectable biopsy marker mass of claim 1, wherein at least a portion of the particles have both internal bubble cavities and have exposed surfaces of broken bubble cavities.

6. An ultrasound-detectable biopsy marker mass which has a detectable in-vivo lifetime during which the marker mass remains readily detectable by ultrasound, and which is formed of particles of a bio-resorbable material having a particle size between about 300 microns and about 500 microns, and at least a portion of the particles having one or more bubble cavities inside a respective particle.

7. The ultrasound-detectable biopsy marker mass of claim 6, the bubble cavities having a size of at least 50 microns, wherein the bubble cavities have geometric centers and the cavity size is measured by length through the geometric centers of the cavities.

8. The ultrasound-detectable biopsy marker mass of claim 6, wherein said bio-resorbable material comprises a bio-resorbable polymeric material.

9. The ultrasound-detectable biopsy marker mass of claim 6, wherein the particles are held together with a binding agent.

10. The ultrasound-detectable biopsy marker mass of claim 6, wherein the respective particle has an exposed surface of at least one broken bubble cavity.

11. A bolus of biopsy marker powder which is ultrasonically detectable in-vivo within a patient's biopsy site for a period of at least two weeks but not longer than six months, which comprises a comminuted bio-resorbable polymeric powdered material, at least 80% of the comminuted powder having particles with a particle size of about 300 to about 800 microns and the particles of the comminuted powder having one or more bubble cavities within the particles smaller than the particle size of the particles.

12. The bolus of biopsy marker powder of claim 11, wherein the particles of the comminuted powder have a particle size between about 300 microns and about 500 microns.

13. The bolus of biopsy marker powder of claim 11, wherein the comminuted powder comprises about 65% by weight polylactic acid and about 35% by weight polyglycolic acid.

14. The bolus of biopsy marker powder of claim 11, wherein the comminuted powder has a bulk density of between about 0.8 g/ml and about 1.5 g/ml.

15. The bolus of biopsy marker powder of claim 11, having an ultrasonically detectable in-vivo lifetime of not greater than about 20 weeks.

16. The bolus of biopsy marker powder of claim 11, having an ultrasonically detectable in-vivo lifetime between about 6 weeks and about 12 weeks.

17. The bolus of biopsy marker powder of claim 11, wherein the particles are held together with a binding agent.

18. The bolus of biopsy marker powder of claim 17, wherein the binding agent is selected from the group consisting of gelatin, polyethylene glycol, polyvinyl alcohol, glycerine, acrylic hydrogels, organic hydrogels, and combinations thereof.

19. The bolus of biopsy marker powder of claim 17, wherein the binding agent is selected from the group consisting of bovine collagen, porcine collagen, ovine collagen, equine collagen, synthetic collagen, agar, synthetic gelatin, and combinations thereof.

20. The bolus of biopsy marker powder of claim 11, comprising one part gelatin and about five parts comminuted bio-resorbable polymeric material, the particles of the comminuted material having bubble cavities about 50 to about 200 microns in size.

21. The bolus of biopsy marker powder of claim 11, comprising about one part gelatin to about three parts polymeric material.

22. The bolus of biopsy marker powder of claim 11, wherein at least a portion of the particles have both internal bubble cavities and have exposed surfaces of broken bubble cavities.

* * * * *